US008814009B2

(12) United States Patent
Hodson et al.

(10) Patent No.: US 8,814,009 B2
(45) Date of Patent: Aug. 26, 2014

(54) METERED DOSE VALVE

(75) Inventors: Peter D. Hodson, Derby (GB); Matthew A. Goring, Clitheroe (GB); Stephen J. Howgill, Thurcaston (GB); John Fielding, Nr Clitheroe (GB); Richard D. Brewer, Loughborough (GB); Rachael V. Shaw, Wymeswold (GB); Paul A. Charnock, Blackburn (GB); Stuart A. McGlasson, Halifax (GB); Stephen D. Helm, Blackburn (GB); Graham V. Jackson, Leicester (GB); Anthony W. Balkwill, Reading (GB); Jason A. Graves, Bracknell (GB)

(73) Assignee: 3M Innovative Properties Company, St. Paul, MN (US)

( * ) Notice: Subject to any disclaimer, the term of this patent is extended or adjusted under 35 U.S.C. 154(b) by 882 days.

(21) Appl. No.: 12/681,280

(22) PCT Filed: Oct. 2, 2008
(Under 37 CFR 1.47)

(86) PCT No.: PCT/US2008/078549
§ 371 (c)(1),
(2), (4) Date: Nov. 15, 2010

(87) PCT Pub. No.: WO2009/046173
PCT Pub. Date: Apr. 9, 2009

(65) Prior Publication Data
US 2011/0042419 A1    Feb. 24, 2011

(30) Foreign Application Priority Data
Oct. 5, 2007  (GB) .................................. 0719416.0

(51) Int. Cl.
*B65D 83/00*    (2006.01)

(52) U.S. Cl.
USPC ................ 222/402.2; 222/402.1; 222/402.24

(58) Field of Classification Search
CPC .... B65D 83/54; B65D 83/425; B65D 83/205; A61M 15/009
USPC ......... 222/402.2, 402.24, 402.1, 402.25, 402; 128/200.23
See application file for complete search history.

(56) References Cited

U.S. PATENT DOCUMENTS 3,117,700 A * 1/1964 Gorman ..................... 222/402.2
3,542,253 A * 11/1970 Weber ........................... 222/398

(Continued)

FOREIGN PATENT DOCUMENTS

GB    1201919      8/1970
GB    2 087 355    5/1982 .............. G01F 11/32

(Continued)

OTHER PUBLICATIONS

International Search Report for PCT/US2008/078549 prepared by the Korean Intellectual Property Office.

*Primary Examiner* — Paul R Durand
*Assistant Examiner* — Jeremy W Carroll

(57) ABSTRACT

An aerosol metering valve comprising: (a) a valve stem movable between a rest position and a firing position comprising: a body portion comprising a circumferential sealing surface (b) a valve body comprising: a body wall, and an internal chamber defined at least in part by the body wall; and (c) a metering gasket having an inner periphery defining an aperture, being disposed near the most interior end of the internal chamber and being configured to be able to form a transient, substantially fluid-tight face seal against the circumferential sealing surface of the valve stem, where at the rest position of the valve stem, the body portion of the valve stem is located within the internal chamber and as the valve stem is moved from its rest position towards its firing position the circumferential sealing surface of the valve stem contacts the metering gasket to form a face seal thereby closing a metering chamber and thereafter further movement of the valve stem towards its firing position causes the metering gasket to deflect while maintaining the seal with the circumferential sealing surface of the valve stem; and wherein the metering gasket in an unbiased configuration is an annular disc having a substantially planar form and where the valve is constructed and arranged such that the inner periphery of the metering gasket is urged out of said substantially planar form at the rest position of the valve stem, or wherein the metering gasket is pre-biased into a dished-shape.

2 Claims, 29 Drawing Sheets

(56) References Cited

U.S. PATENT DOCUMENTS

| | | | |
|---|---|---|---|
| 3,741,446 A * | 6/1973 | Marand | 222/402.24 |
| 4,413,755 A | 11/1983 | Brunet | |
| 4,441,634 A * | 4/1984 | Meshberg | 222/402.16 |
| 4,944,433 A | 7/1990 | Knecht et al. | |
| 4,982,900 A * | 1/1991 | Blake | 239/333 |
| 5,490,497 A * | 2/1996 | Chippendale et al. | 128/200.14 |
| 5,772,085 A | 6/1998 | Bryant et al. | |
| 6,622,893 B2 * | 9/2003 | Leone et al. | 222/402.2 |
| 6,880,733 B2 | 4/2005 | Park | |
| 6,978,915 B1 | 12/2005 | Russell | |
| 7,234,460 B2 * | 6/2007 | Greenleaf et al. | 128/200.23 |
| 7,299,801 B2 * | 11/2007 | Hodson | 128/200.23 |
| 2003/0121935 A1 * | 7/2003 | Arsenault et al. | 222/1 |
| 2003/0192917 A1 * | 10/2003 | Eames et al. | 222/402.1 |
| 2005/0183720 A1 * | 8/2005 | Di Giovanni et al. | 128/200.23 |
| 2008/0023000 A1 * | 1/2008 | Fenn et al. | 128/200.23 |

FOREIGN PATENT DOCUMENTS

| | | |
|---|---|---|
| WO | 2004/022142 | 3/2004 |
| WO | 2008/014161 | 1/2008 |

* cited by examiner

METERED DOSE VALVE

CROSS REFERENCE TO RELATED APPLICATIONS

This application is a national stage filing under 35 U.S.C. §371 of PCT/US2008/078549, filed Apr. 9, 2009, which claims priority to Great Britain Application No. 0719416.0, filed Oct. 5, 2007, the disclosure of which is incorporated by reference in its/their entirety herein.

FIELD

The present invention relates to an aerosol metering valve, especially, although not exclusively, intended for use as a valve for a pressurized metered dose inhaler (pMDI).

BACKGROUND

One form of valve for a pMDI is described in WO-A-04/22142, which discloses an aerosol metering valve comprising:

(a) a valve stem that generally defines a longitudinal axis and comprises:
  (1) a body portion comprising a proximal end, a distal end, and at least one side surface connecting the proximal end and the distal end and comprising a metering surface, wherein the longitudinal axis and a plane tangential to at least a portion of the metering surface define an angle from about 2° to about 90°, and
  (2) a stem portion comprising a discharge passageway;
(b) a valve body comprising:
  (1) a body wall that comprises a sealing portion,
  (2) an internal chamber defined at least in part by the body wall and comprising a metering portion configured to substantially conform to the metering surface of the valve stem, and
  (3) a diaphragm having walls that define an aperture in slidable, sealing engagement with the stem portion of the valve stem; and
(c) a metering gasket configured to be able to form a transient, substantially fluid-tight face seal between the valve stem, in particular the body portion of the valve stem, and the sealing portion of the body wall. As the valve stem moves from its rest position towards its firing position a surface of the body portion of the valve stem contacts the metering gasket to form a face seal thereby closing a metering chamber and thereafter further movement of the valve stem to its firing position causes the metering gasket to deflect while maintaining the seal with the aforementioned surface of the valve stem. At the rest position of the valve stem, the metering gasket is not in contact with the valve stem.

GB 1201919 discloses an aerosol metering valve having two annular seals made from elastomeric sheet material and which are constrained to adopt conical configurations when assembled into the valve. Constraining the seals in this way prevents them dishing inwardly upon operation of the valve. The seals are not caused to deflect while maintaining a seal with the valve stem upon movement of the valve stem towards its firing position.

SUMMARY OF THE INVENTION

This application is concerned with metered aerosol valves employing an annular seal operating as a face seal against a valve stem with a portion which passes into the opening in the annular seal having a diameter greater than that of the opening. It is especially applicable to such valves for dispensing pressurized product i.e. product formulated with a propellant.

It has not previously been appreciated that if such a seal (e.g., such a seal that comes in and out of contact with the valve stem during operation of the valve) is only constrained about the region of its outer circumference (e.g. by an annular crimp compressing the faces of the seal towards each other or by confining the outer periphery of the seal compressively about its circumference), it may not locate as intended and/or it may adopt inconsistent positional modes when it returns to its rest position.

For example, when employed as a metering gasket under the above conditions, the metering gasket can flip into an up or down orientation, i.e. it can exhibit bistable (bimodal) behaviour. Because the point at which the metering gasket first seals off against the valve stem may define a metered volume of medicament formulation, such positional inconsistency has the potential to cause unwanted shot weight inconsistencies and hence poor control of dose metering.

Without wishing to be bound by any theory, it is believed that such a metering gasket can have uncontrolled compressional stresses in its inner region which can under certain circumstances cause such flipping of the metering gasket into an up or down orientation in a fairly random manner both between valves and between actuations of a single valve.

It appears that the inner region of the metering gasket tends to get compressed radially inwards during valve assembly or crimping, and that varying seal compression (e.g. due to seal thickness variation or other component dimensional variation or crimp inconsistencies) occurs between units. This causes the bimodal behaviour referred to above, which can manifest itself in widely varying and/or bimodal valve shot weights.

The present invention aims to address this problem by forcing the metering gasket to return to a single positional mode when the valve stem is in its rest position.

Accordingly, there is provided an aerosol metering valve comprising:

(a) a valve stem movable between a rest position and a firing position comprising:
  a body portion comprising a circumferential sealing surface
(b) a valve body comprising:
  a body wall, and
  an internal chamber defined at least in part by the body wall; and
(c) a metering gasket having an inner periphery defining an aperture, being disposed near the most interior end of the internal chamber and being configured to be able to form a transient, substantially fluid-tight face seal against the circumferential sealing surface of the valve stem,
where at the rest position of the valve stem, the body portion of the valve stem is located within the internal chamber and as the valve stem is moved from its rest position towards its firing position the circumferential sealing surface of the valve stem contacts the metering gasket to form a face seal thereby closing a metering chamber and thereafter further movement of the valve stem towards its firing position causes the metering gasket to deflect while maintaining the seal with the circumferential sealing surface of the valve stem; and
wherein the metering gasket in an unbiased configuration is an annular disc having a substantially planar form and where the valve is constructed and arranged such that the inner periphery of the metering gasket is urged out of said substantially planar form at the rest position of the valve stem, or wherein the metering gasket is pre-biased into a dished-shape.

Such aerosol metering valves are advantageous in that the metering gasket is biased into a single asymmetric positional mode. Such biasing into a single asymmetric positional mode is particularly advantageous for valves where the metering gasket is not in contact with the valve stem when the valve stem is in its rest position.

Again when the valve stem is in its rest position, relative to the nominal plane perpendicular to a longitudinal axis defined by the valve stem and through the center of the outermost periphery of the metering gasket, the center of the innermost periphery of the metering gasket is favorably at least 0.2 mm (more favorably at least 0.5 mm) out of said nominal plane.

Also for enhanced single positional stability and/or further reduction of any potential for bimodal behavior, it is desirable to construct and arrange the valve such that the outer periphery of a major surface of the metering gasket is pulled radially outwards into tension.

At the rest position of the valve stem, the metering gasket may be biased inwardly (i.e. with the inner periphery of the metering gasket positioned away from the body portion of the valve stem) or outwardly (i.e. with the inner periphery of the metering gasket positioned towards the body portion of the valve stem). For enhanced positional stability and/or avoidance of a potential for bimodal behavior, preferably the metering gasket is biased inwardly. Such preferred valves where the metering gasket is biased inwardly are particularly advantageous when the valve is configured and arranged such that during routine operation of the valve the metering gasket will not move into a substantially planar position (and consequently will not move through such a substantially planar position into an outward position).

Valves in accordance with the present invention use a metering gasket, which forms a face seal during actuation and which is advantageously held in a stable deformed configuration when the valve stem is at rest, allowing for a return of the metering gasket to a consistent position when the valve stem returns to the rest position.

This is particularly advantageous for pMDI valves of the type described in WO.A-04/22142 in which the action of depressing the valve stem causes the formation of a transient metering chamber. Accordingly preferred embodiments of valves described herein are constructed and arranged as to allow the formation of a transient metering chamber upon depression of the valve stem. In particular in such valves, the valve stem further comprises a stem portion having a discharge passageway, the valve body further comprises a diaphragm having walls that define an aperture in slidable, sealing engagement with the stem portion of the valve stem and wherein the body portion of the valve stem further comprises a metering surface, the metering surface being configured and arranged near the stem portion such that at the rest position of the valve stem, a substantial portion of the metering surface rests in contact with an interior surface of the valve body and/or an interior surface of the diaphragm and as the valve stem is moved from its rest position towards its firing position a metering chamber is formed between said interior surface(s) and said metering surface of the valve stem, the volume of the metering chamber increasing as the valve stem is displaced until the circumferential sealing surface of the valve stem contacts the metering gasket to form a face seal thereby closing the metering chamber and thereafter further movement of the valve stem allows an opening of the discharge passageway in the stem portion of the valve stem to pass through the diaphragm into fluid communication with the metering chamber. Such preferred embodiments provide certain advantages over existing marketed valves, including desirably consistent metering volumes and thus metered doses (including minimization or avoidance of loss of prime) as the result of inter alia using a metering gasket as described herein and a metering chamber that is formed upon actuation and which can fill and empty easily. Such fast-fill-fast-empty characteristics may be further facilitated through the use of a metering gasket having a large aperture (e.g. about 3 mm or more in diameter).

BRIEF DESCRIPTION OF THE DRAWINGS

The present invention will now be explained in more detail by way of the following description of preferred embodiments and with reference to the accompanying drawings, in which:

FIG. 3A shows a cross-section through part of a first embodiment of an exemplary valve according to the present invention, while

DETAILED DESCRIPTION

Figure 1:
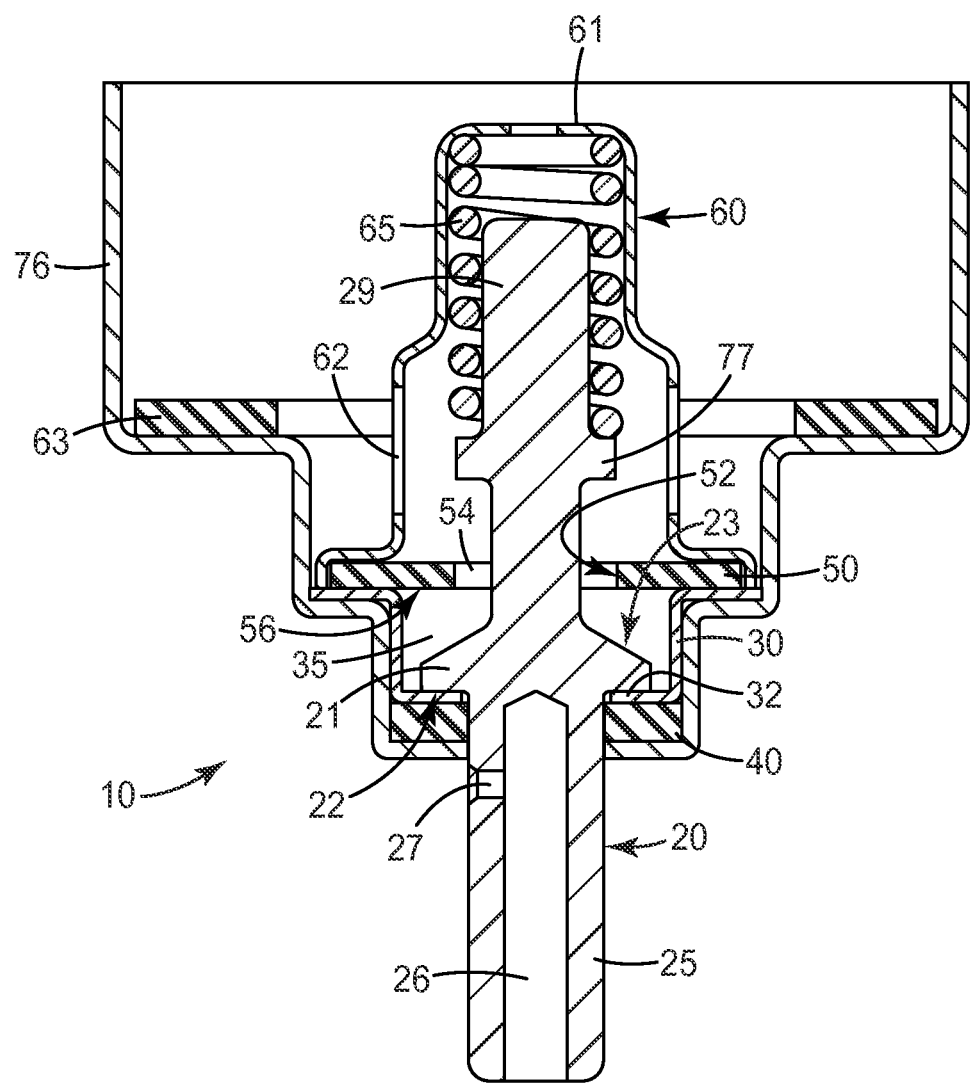
FIG. 1 shows a view in partial cross-section of one known form of a valve having a deflecting face seal.
Figure 2:
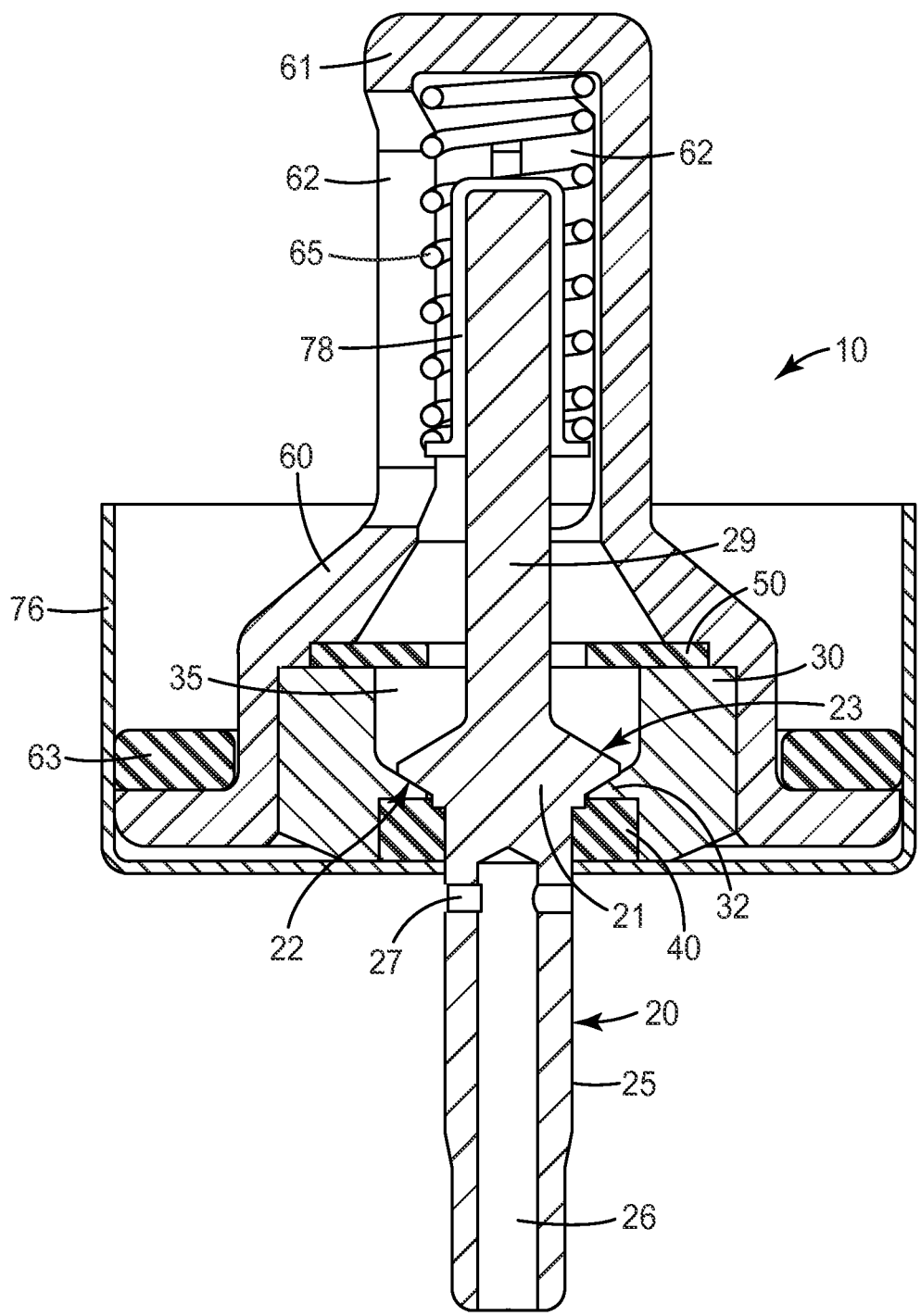
FIG. 2 shows a view in partial cross-section of a further known form of valve having a deflecting face seal.

FIGS. 1 and 2 of the accompanying drawings illustrate aerosol valves of the type generally disclosed in WO 04/022142. The features of the valves in FIGS. 1 and 2 are similar and like reference numerals refer to like parts. The valve of FIG. 1 is designed for the valve stem, valve body and spring cage components to be constructed of metal, preferably stainless steel. The design of FIG. 2 allows these components to be made of plastics materials. FIGS. 3 to FIG. 23 illustrate exemplary aerosol valves in accordance with the present invention where again like reference numerals refer to like parts. For a better understanding of the present invention, in the following, common features of embodiments described herein will be first described, typically in reference to the embodiment shown in FIG. 4.

Figure 3A:
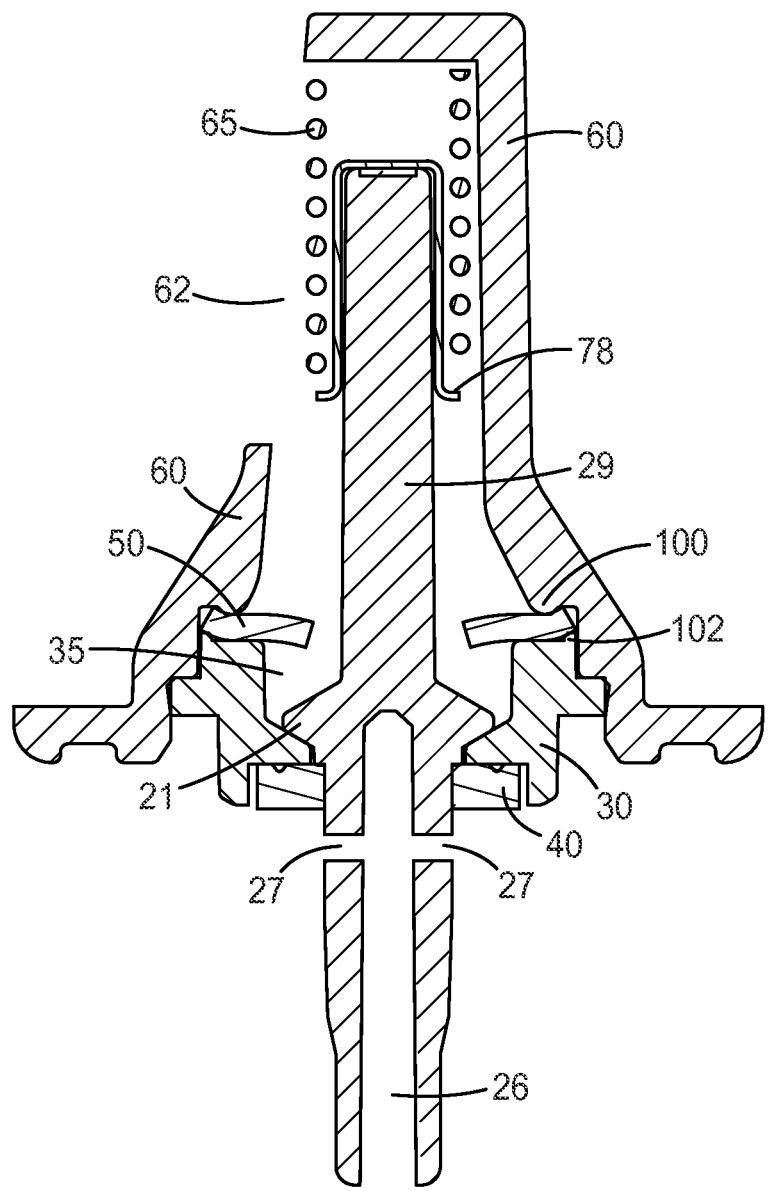
Figure 3B:
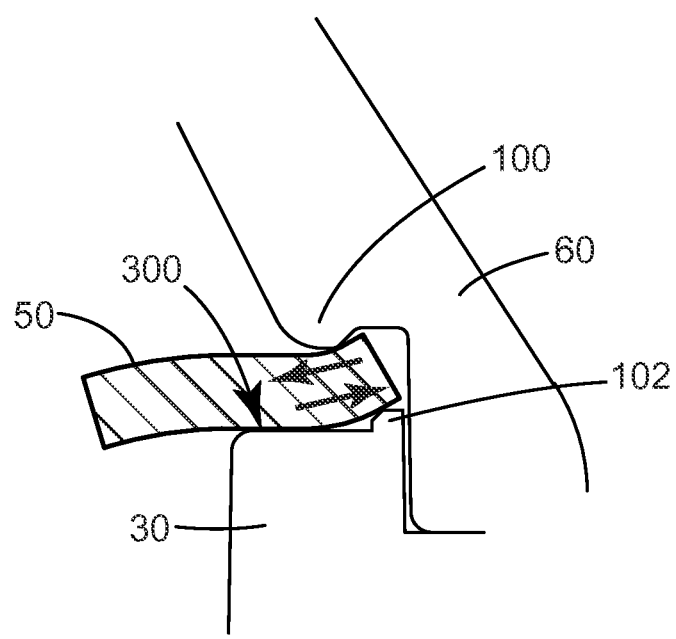
FIG. 3B shows a detailed cross-section of a portion of the metering gasket and surrounding valve components.
Figure 4:
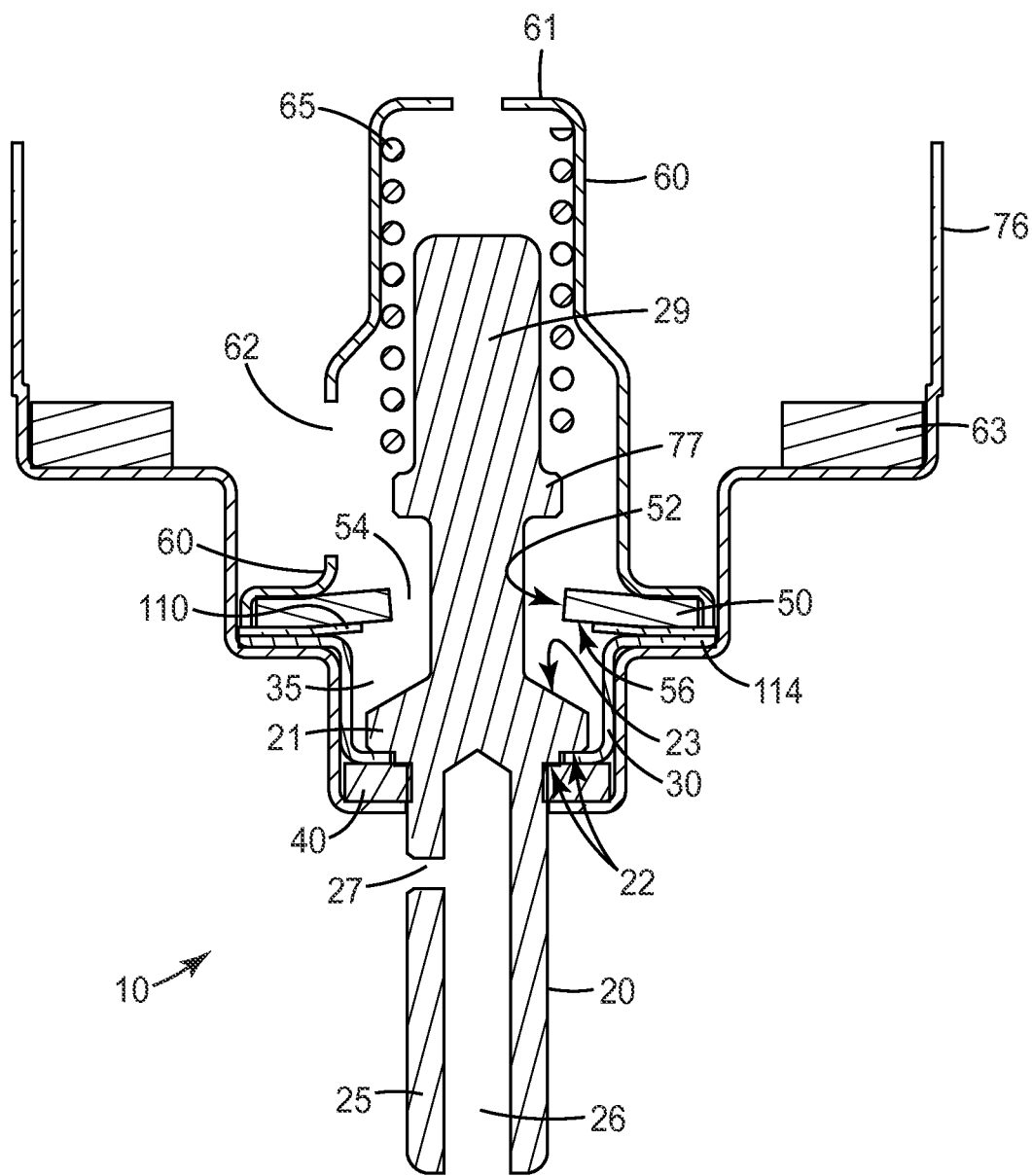
FIG. 4 shows a cross-section through a second embodiment of an exemplary valve according to the present invention.

Referring to FIG. 4, aerosol valves (10) described herein typically comprise a valve ferrule (76) that allows the valve to be secured to an aerosol container (not shown) by crimping the circumferential flange around a lip on the aerosol container with a gasket (63) making a fluid tight seal. Referring to the orientation of the valves shown in the illustrations, the aerosol container would extend upwardly. Although the embodiments in FIGS. 3, 5, 6, 7, 9 to 14, 16, 19, and 22 are shown without a ferrule and ferrule gasket, these embodiments would also typically include a ferrule. The ferrule also typically serves to support the valve components. Here the ferrule is typically provided with one or more circumferential crimps to secure inner valve components. This can be best seen in reference to FIG. 20, where the position of such a crimp (99) that is used to hold certain valve component together is shown. Similar crimping is used (but is not shown) in all the other valve embodiments shown herein.

Referring to FIG. 4, aerosol valves described herein comprise a valve body (30) having a body wall, with an internal chamber (35) defined at least in part by the body wall. Aerosol valves described herein comprise a metering gasket (50). The metering gasket is typically made of an elastomeric material. However in certain embodiments of the present invention, the metering gasket is made of a shape memory polymer, in particular a shape-memory elastomer. As can be appreciated e.g. from the embodiment shown in FIG. 4, the metering gasket is disposed near the most interior end of the internal chamber. The metering gasket (50) comprises an inner periphery (52) defining an aperture (54).

Valves described herein also comprise a valve stem (20) comprising a body portion (21), the body portion being located within the internal chamber when the valve stem is in its rest position. The body portion of the valve stem has a circumferential sealing surface (23). Generally the body portion is favorably configured as a circumferential flange having a lower surface (22), also termed a metering surface. The valve stem typically includes a stem portion (25) which is provided with a discharge passageway (26) in communication with a side hole (27). The valve typically includes a diaphragm seal (40), typically made of an elastomeric material, that has walls defining an aperture in slidable sealing engagement with the stem portion (25) of the valve stem. In the embodiments of FIGS. 5, 6, 7, 9 to 14, 16, 19, and 22 the diaphragm seal is not shown; these embodiments like the embodiment in FIG. 4 will typically include a diaphragm seal.

To allow for the provision of a transient face seal during operation of the valve, the diameter at some position on the body portion of the valve stem is greater than the diameter of an aperture in the metering gasket, so that when that position meets the metering gasket and then moves further inwardly, it causes a face seal to be formed between the valve stem and the metering gasket and then deflection of the metering gasket, respectively. As can be appreciated from illustrative valves, deflection of the metering gasket while maintaining a seal with the circumferential sealing surface of the valve stem typically involves some sliding contact between the respective surface of the metering gasket and the circumferential sealing surface of the valve stem. However this sliding contact is not co-linear with the axis of the valve stem. Moreover the deflecting face-sealing engagement between the circumferential sealing surface of the valve stem and the metering gasket in the valves described herein is advantageously not a co-linear sliding type sealing engagement used in conventional pMDI valves. This is advantageous for a number of reasons include avoidance of frictional and concentricity issues associated with some conventional, commercial pMDI valves. Further to allow for the provision of a transient face seal during operation of the valve and at the same a large opening into the interior of the valve, the valve stem typically has a body portion that has a wider diameter than the stem portion. Generally, the circumferential sealing surface may be angled relative to the axis of the valve, such that a plane tangential to it defines an angle of about 30° to about 80° with respect to the axis of the stem (as described in WO 04/24122 page 10 and shown in FIG. 10 therein). Within this range, a minimum angle of about 35° is more desirable and about 40° most desirable. A maximum angle of about 75° is more desirable and about 70° most desirable. In some embodiments, the angle θ may be defined by the intersection of the central axis and a plane tangential to a major portion of the circumferential sealing surface. For embodiments in which the circumferential sealing surface is only generally conical in form and with concave sides in its longitudinal cross-section, angles of θs may be defined along the entire concave surface by the intersection of the central axis and planes tangential to the curved surface; the values of these angles are desirably all within the ranges defined above.

Again referring to FIG. 4, in the aerosol valves described herein, the valve stem may include a second stem portion (29) extending through the aperture (54) in the metering gasket (50). For the sake of clarity in the following, such a second stem portion will be referred to as the upper stem portion, while the stem portion in slidable, sealing engagement with the diaphragm will be referred to as the lower stem portion.

If the valve stem is provided with an upper stem portion, desirably the configuration of this upper stem portion is such that it does not contact the metering gasket, and the diameter of this upper stem portion is such that, at the rest position of the valve stem, a large opening is maintain between the valve stem and inner edge of the metering gasket. Favorably the aperture of the metering gasket is considerably larger than the cross section of the upper stem portion of the valve stem near the gasket (50) when the valve stem is in its rest position and during filling, in order to facilitate easy passage of the aerosol formulation into the interior of the valve. Typically the general form of the aperture provided in the metering gasket in its horizontal cross-section is shaped to match the general form of circumferential sealing surface of the body portion of the valve stem in its horizontal cross-section. Moreover typically the circumferential sealing surface is generally conical, and thus the aperture is also usually circular. For embodiments including an upper stem portion extending through the aperture of the metering gasket, the size of aperture and thus the size of opening into the interior of the valve is typically selected and configured so as to maintain fast-fill-fast-empty characteristics. Generally the diameter of the aperture in the metering gasket is at least about 3 mm and more favorably at least about 3.5 mm. The diameter of the aperture may be as large as about 9 mm, but favorably it is at most about 6 mm, and more favorably the diameter of the aperture is in the range from about 3.5 to about 5 mm. If the aperture is not circular, the size of the aperture should generally be of comparable area to that calculated from the above diameters.

Again referring to the exemplary embodiment shown in FIG. 4, typically the valve stem in the valves described herein is biased into its rest position by a spring (65) contained within a spring cage (60). Typically the spring cage comprises one or more openings (62) that allow ready passage of the contents of the aerosol container into the interior of the valve. Typically, each hole has an area in the range 1.5 $mm^2$ to 8 $mm^2$. Preferably there are three or four such holes in the spring cage, more preferably four. Typically one end of the spring (65) abuts the end (61) of the spring cage, and the other end of the spring acts on a projection (77) on the upper valve stem portion (29) or alternatively on a component (e.g. a spring guide) provided on the upper stem portion.

As can be appreciated from FIG. 4, typically at the rest position of the valve stem a substantial portion of the lower, metering surface of the body portion of the valve stem rests in contact with an interior surface of the valve body (or alternatively, depending on the particular configuration of a valve, in contact with an interior surface of the diaphragm seal or interior surfaces of both the valve body and diaphragm seal). In the embodiment shown in FIG. 4, the lower, metering surface (22) is in two parts, one contacting each of an interior surface of the diaphragm seal and an interior surface of the valve body. Upon actuation of the valve, a metering chamber (45, not visible) is formed generally between the lower, metering surface (22) of the body portion of the valve stem and said interior surface(s). (The metering chamber is not visible in any of the Figures, since the valves are shown in their rest position.) Moreover in operation, the valve stem (20) is moved inwardly (upwardly with respect to the valve orientation shown in the Figures) against the bias of the spring. As the valve stem is moved from its rest position towards its firing position a metering chamber is formed, the volume of the metering chamber increasing as the valve stem is displaced inwardly. Aerosol formulation may flow readily beneath the lower, metering surface of the body portion of the valve stem into the thus formed metering chamber. As the valve stem moves inwardly a position is reached where the circumferential sealing surface (23) of the valve stem forms face seal engagement with the metering gasket (50), thereby closing off the metering chamber and thus preventing passage of aerosol formulation to or from the metering chamber. As will be appreciated from the exemplary valves described herein, the face seal that is formed when the circumferential sealing surface of the valve stem contacts the metering gasket during actuation of the valve is typically the first seal to be formed between the two respective components. Prior to the formation of the face seal, the two respective components are typically not in contact at all. At the point in time when the initial sealing contact is made, the side hole (27) is still sealed from the metering chamber (45) by the diaphragm (40). Further inward movement of the valve stem causes the metering gasket (50) to flex inwardly with its lower major surface (56) maintaining sealing engagement with the circumferential sealing surface (23) of the valve stem. When the valve stem has moved sufficiently for the side hole (27) to pass through the diaphragm into fluid communication with the metering chamber, the contents of the metering chamber are expelled through the discharge passage (26) via the side hole (27).

In the known valves illustrated in FIGS. 1 and 2, the metering gasket (50) is an annular disc in planar form having a central aperture. In the rest position of the valve, the metering gasket is unbiased and is configured to be in a planar position, i.e. perpendicular to the axis of the valve stem.

Features of valves with which the present invention is concerned relate to the metering gasket, in particular the configuration or positioning of the metering gasket within the valve. As described above, upon actuation of the valve a transient metering chamber is formed and the formation of the face seal between the metering gasket and the circumferential sealing surface of the body portion of the valve stem isolates the contents of the metering chamber from the bulk formulation in the aerosol container. Thus the point at which closure occurs defines the metering chamber volume and hence the dose of formulation to be dispensed. If the metering gasket is located at a slightly higher position (more inward position) or is domed inwardly, then the circumferential sealing surface of the valve stem will have to travel further inwardly before a seal is made and the metering chamber is closed off. The metered dose will thus be larger. Conversely, if the metering gasket is located at a slightly lower position (more outward position), or bows outwardly, then the volume of the metering chamber and hence the dose will be smaller. Positional control of the metering gasket thus plays a major role in determining the delivered dose, and typically consistency between valves as well as between individual shots of one valve is very important.

In embodiments in accordance with the present invention the metering gasket is advantageously biased inwardly or outwardly. In other words in valves in accordance with the present invention, the metering gasket is not positioned and/or configured to be in a completely planar position, i.e. the metering gasket is not positioned and/or configured to be completely perpendicular to the axis of the valve stem, at the rest position of the valve. Moreover at the rest position of the valve, relative to a nominal plane perpendicular to the axis of the valve stem and through the center of the outermost periphery of the metering gasket, the metering gasket is advantageously positioned and/or configured in the valve so that the center innermost periphery of the metering gasket is out of the said nominal plane. Favorably the inner periphery is at least 0.2 mm (more favorably at least 0.5 mm) out of said nominal plane. Said inner periphery may be above or below said plane, and thus in reference to the orientation of the exemplary valves as shown in FIGS. 3 to 23, inwardly or outwardly. It will be appreciated by the skilled reader that in reference to the normal positioning of a metering valve affixed onto an aerosol container, "outwardly" generally means away from the aerosol container (or towards the body portion of the valve stem) and "inwardly" generally means towards the aerosol container (or away from the body portion of the valve stem). Furthermore, the metering gasket is advantageously biased in said inward or outward position. Biasing can be achieved by form-biasing, i.e. the metering gasket is pre-biased into a dished-shape, desirably made from a shape-memory polymer, in particular a shape memory elastomer. Biasing can also be achieved through mechanical biasing, i.e. through the use of a metering gasket that in its unbiased configuration is an annular disc having a substantially planar form, where the valve is constructed and arranged such that when the valve is in its rest position the inner periphery of the metering gasket is urged out of said substantially planar form.

Again when the valve stem is in its rest position, relative to the nominal plane perpendicular to a longitudinal axis defined by the valve stem and through the center of the outermost periphery of the metering gasket, the center of the innermost periphery of the metering gasket is favorably at least 0.2 mm (more favorably at least 0.5 mm) out of said nominal plane.

FIG. 3A illustrates in longitudinal cross-section one way in which the metering gasket can be made to adopt a single, mono-stable position in accordance with the invention. In FIG. 3A, an arrangement of parts of the spring cage (60) and valve body (30) is shown in partial longitudinal cross-section. The spring cage (60), valve body (30) and stem (20) shown in this embodiment of the invention have a form suitable to be made by injection moulding of a plastics material. (Although not shown, the embodiment shown in FIG. 3 would include a valve ferrule.) FIG. 3B shows schematically a detailed view of a portion of the metering gasket (the right hand side) and the surrounding portions of the valve that is illustrated in FIG. 3A. The spring cage (60) and the valve body (30) are provided with protruding annular ribs (100, 102, respectively) that apply shear forces (represented by the two bold opposing arrows) to the metering gasket (50), causing it to bend outwardly. Thus, the metering gasket (50), which in an unbiased configuration has an annular planar configuration, is biased out of its planar configuration. An edge (300) on the valve body defines the maximum extent of that bend, hence defining its position accurately and consistently. The configuration of the two ribs that grip the metering gasket is advantageously designed to prevent "walk-out" i.e. the radially inward motion of the metering gasket under the action of pressure filling and/or repeated stem flange contact. The ribs (100, 102) may be optimised to put tension into the inner region of the metering gasket. The rib (102) on the valve body stretches the outer edge of the metering gasket into the recess on the underside of the spring cage, thereby stretching the whole metering gasket and thereby avoiding or reducing any compressive stresses near the inner edge of the metering gasket. An absence or reduction of compressive stresses there avoids or reduces the risk of unwanted metering gasket positional bimodality and of crinkling, etc. The ribs can have any suitable geometry, e.g. they could be sharp-edged sealing beads.

FIG. 4 illustrates another design that causes the metering gasket (50) to adopt a single positional mode. An angled washer (110) is positioned between the valve body (30) and the metering gasket (50), and the washer pushes the metering gasket inwardly.

It is preferred to bias the metering gasket inwardly. Directing the metering gasket inwardly (e.g. as shown in FIG. 4) rather than outwardly (e.g. as shown in FIG. 3) means that the metering gasket during routine operation of the valve will not pass into a position in which the metering gasket is "planar" or in a "neutral" position, i.e. perpendicular to the axis of the valve stem (and consequently the metering gasket will also not move through such a neutral position into an outward position during routine operation of the valve). This is advantageous in that this ensures that the metering gasket does not reach a meta-stable position in which the metering gasket might or might not "go over centre" and flip into an opposite position (e.g. an outward position). Thus biasing the metering gasket inwardly, as shown in the exemplary embodiment shown in FIG. 4 and other embodiments described herein, confers yet further stability on the metering gasket and thus on the whole seal movement process. It will be noted that this arrangement also tends to tension the inner regions of the metering gasket, thereby reducing any tendency to buckling, crinkling or positional bistability as a result of compressive hoop stresses around the central hole.

Figure 25:
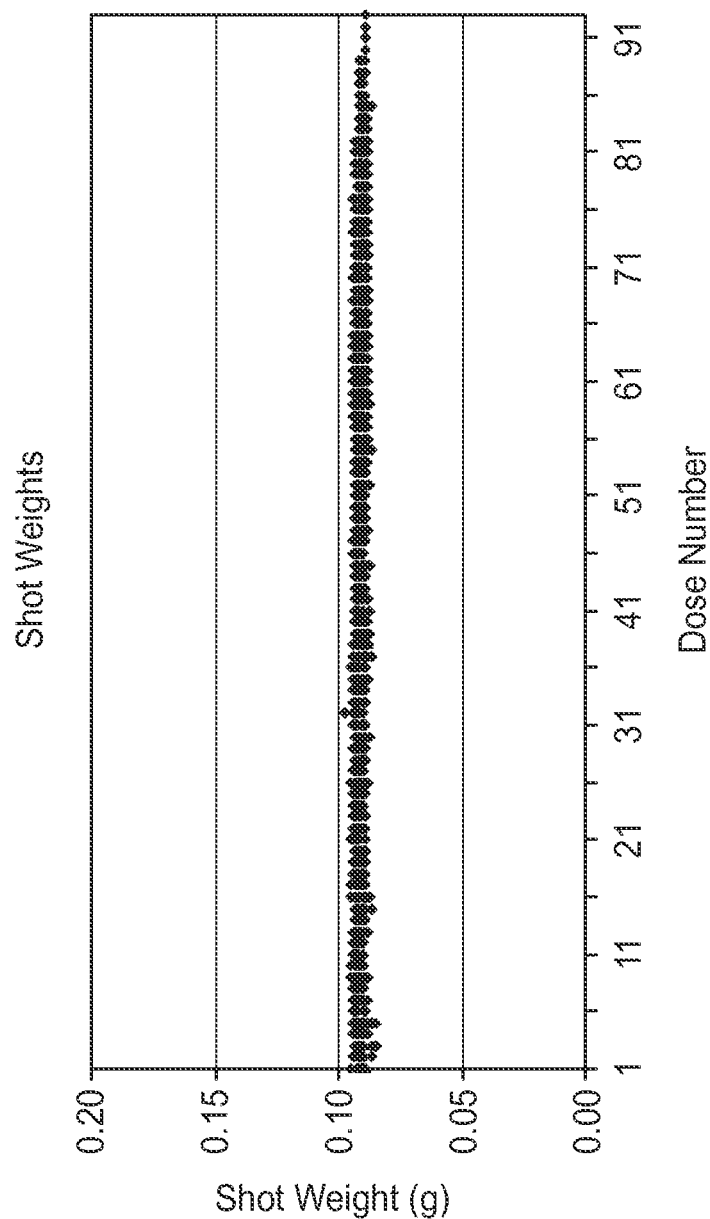
FIG. 25 shows shot weight data from valves having the form of construction of the second embodiment of the present invention as shown FIG. 4.

Referring to the embodiment shown in FIG. 4, the precise geometry of the washer can be optimized (e.g. angled, curved, different dimensions). In one preferred embodiment the washer is made from stainless steel of 0.005" (0.13 mm) thickness, having an outer diameter of 0.427" (10.8 mm) and an inner diameter of 0.207" (5.3 mm), and with the part of the washer within a diameter of 0.300" (7.6 mm) being angled at approximately 6° upwards (inwards in the valve) from that diameter. (All dimensions are approximate.) Although this embodiment theoretically has a potential transient leakage path between the upper flange (114) of the valve body and the lower face of the washer during actuation of the valve, surprisingly valves made according to the embodiment shown in FIG. 4, with washers having the approximate dimensions stated above, showed no such leakage. Data from such valves are shown in FIG. 25. In an alternative embodiment (not shown), the washer is perforated (e.g. as a mesh, with 0.5 mm holes), in order to improve the valve's pressure filling capabilities. The holes provide a greater surface area for the formulation injection pressure to operate over, giving more reliable transient extra deflection of the metering gasket inwardly during pressure filling of the aerosol container.

Figure 5:
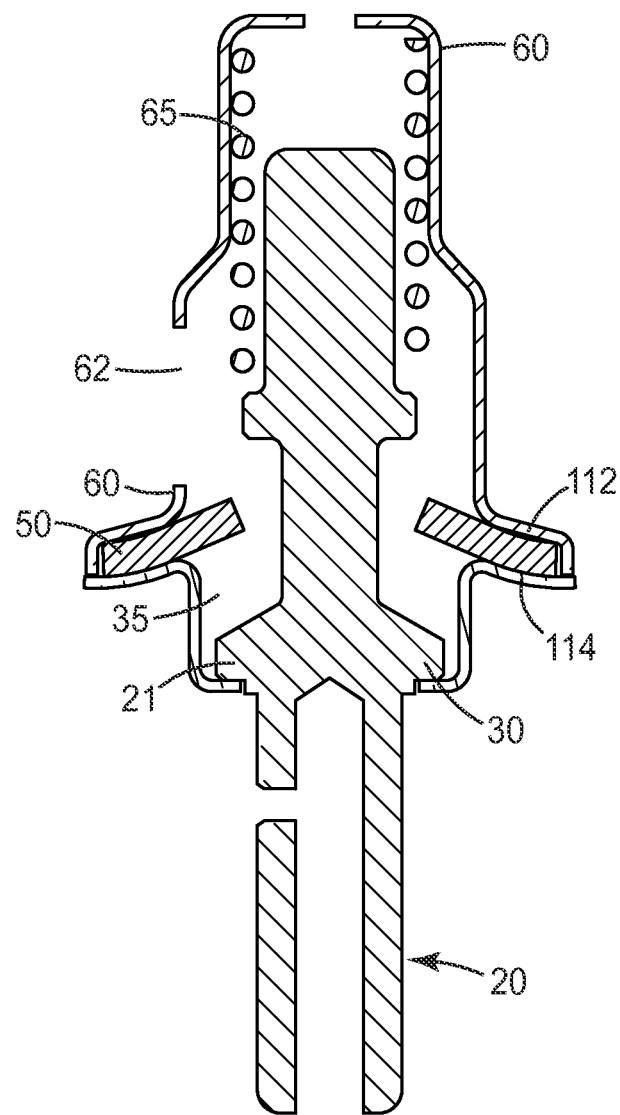
FIG. 5 shows a cross-section through part of a third embodiment of an exemplary valve according to the present invention.

FIG. 5 shows another embodiment, in which the spring cage (60) and the valve body (30) are provided with curved (i.e. in longitudinal cross-section) flanges (112, 114, respectively), the former only very slightly curved; the curved flanges being constructed and arranged to bias the metering gasket (50) inwardly in a similar manner to that shown in FIG. 4, but without the inclusion of a separate washer component. This embodiment saves a component, and its assembly is easier compared with that of the embodiment of FIG. 4, and serves to eliminate a theoretical transient leakage path.

As mentioned above it is to be noted that FIG. 5 is incomplete, showing only the valve body (30), spring cage (60), stem (20), spring (65) and metering gasket (50) components. Other valve components, such as the ferrule, ferrule gasket and diaphragm are not shown. The same holds true for the embodiments shown in FIGS. 6, 7, 9 to 14, 16, 19, and 22.

Figure 6:
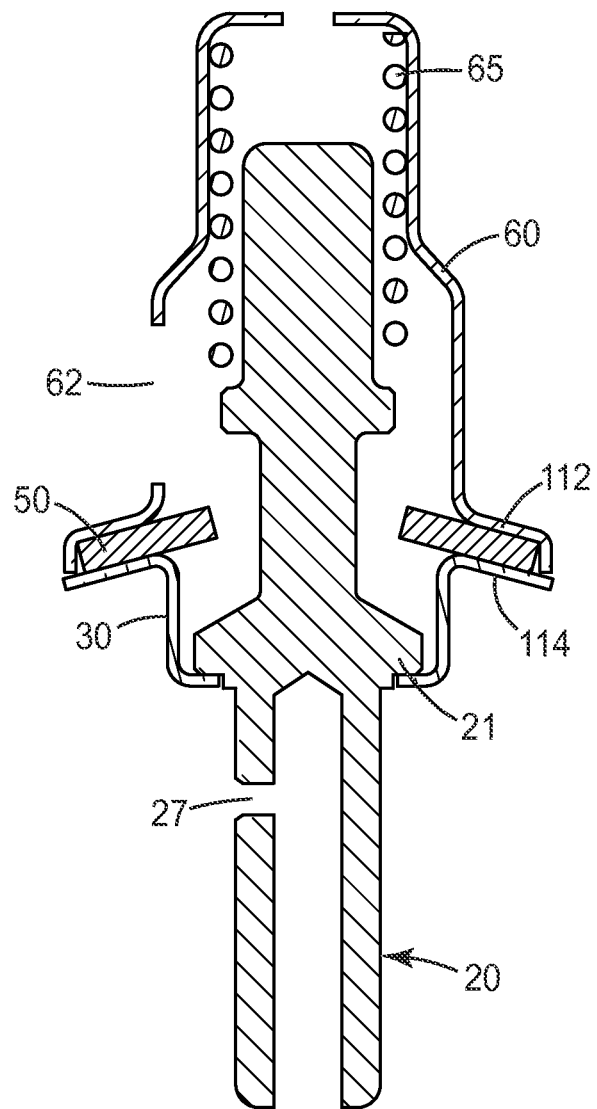
FIG. 6 shows part of a variation of the third embodiment.

FIG. 6 shows a variation on the embodiment of FIG. 5, with angled (i.e. in longitudinal cross-section) flanges (112, 114), rather than curved flanges, on the spring cage (60) and the valve body (30). In reality, the flanges are frusto-conical in three dimensions.

Figure 7:
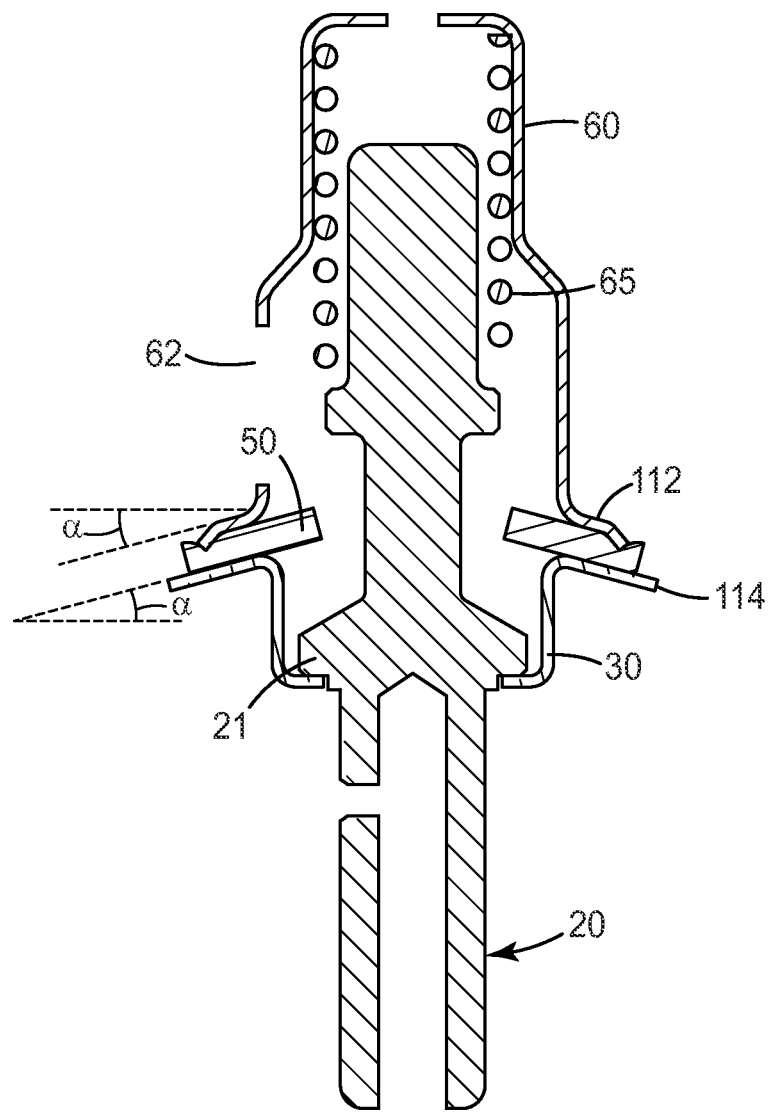
FIG. 7 shows a cross-section through part of a fourth embodiment of an exemplary valve according to the present invention.

FIG. 7 illustrates a design that pulls the metering gasket (50) into tension. As the (e.g. metal) valve is crimped together, the edge of the rim of the flange (112) on the spring cage digs into the metering gasket pulling it down the slope of the flange (114) of the valve body (30) and thereby stretches the metering gasket. Different angles ($\alpha$) of the conical spring cage and valve body flange surfaces (e.g. 5°, 10°, 15°, 20° may be used. In a variation (not shown) of this embodiment, the spring cage flange may have projections, e.g. castellations or crenellations, folded round to grip the seal and with intermediate parts of the flange digging into the top of the seal.

Figure 8A:
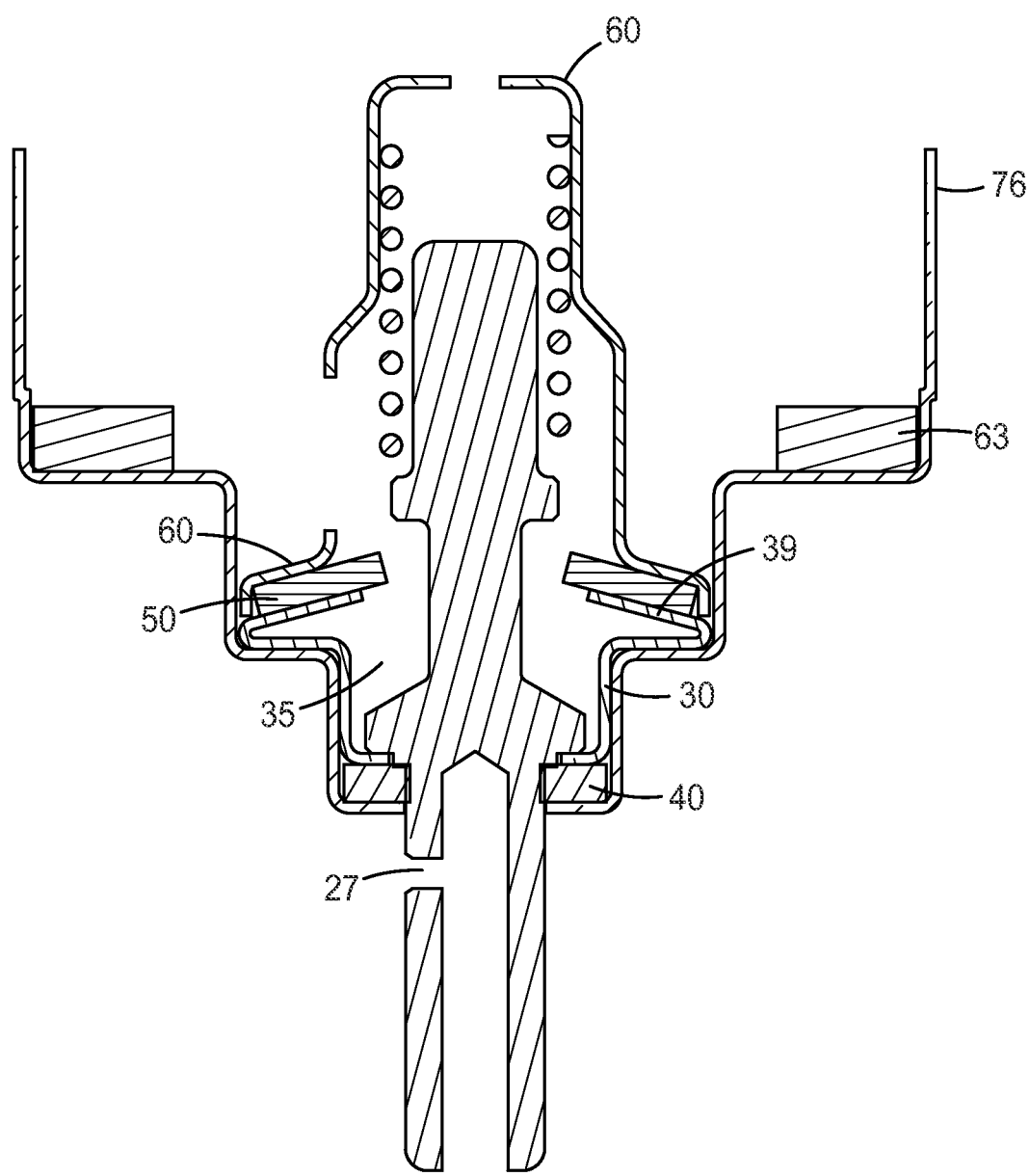
FIGS. 8A and 8B show cross-sections through two variations of a fifth embodiment of an exemplary valve according to the present invention.
Figure 8B:
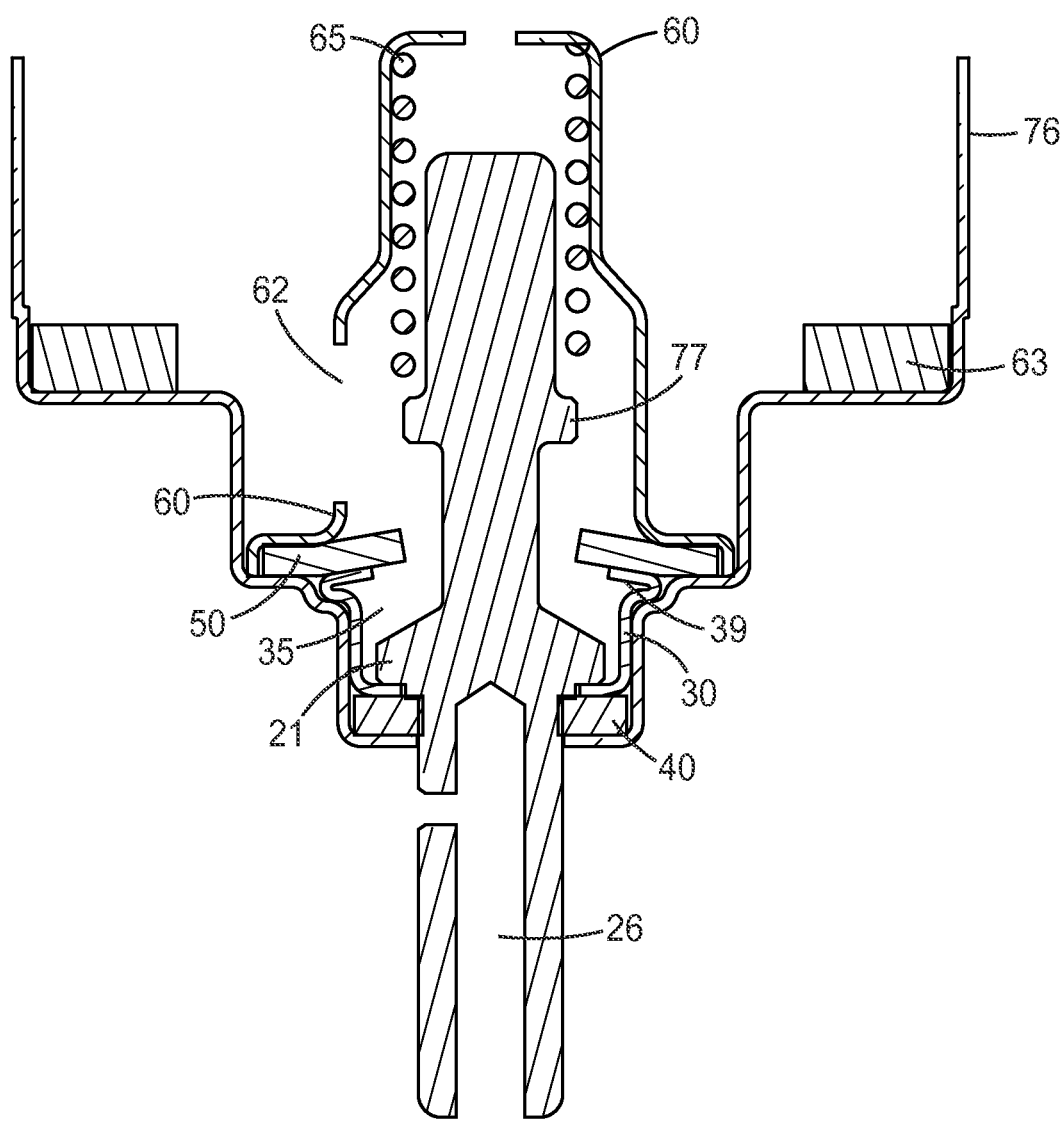

FIG. 8A shows another embodiment that holds the metering gasket reliably and consistently inwardly (again without the need for the extra washer component as shown in the embodiment of FIG. 4). The embodiment comprises a deep drawn metal valve body (30) provided with an upper flange (39) to support and direct the inner region of the metering gasket inwardly. FIG. 8B shows a variation on the embodiment of FIG. 8A, with a valve body (30) provided with a smaller upper flange (39). In further variations of these embodiments (not shown), the upper flanges (39) may be positioned at an angle rather closer to a plane perpendicular to the longitudinal axis of the valve stem, e.g. at an angle of 5° to such a plane.

Figure 9:
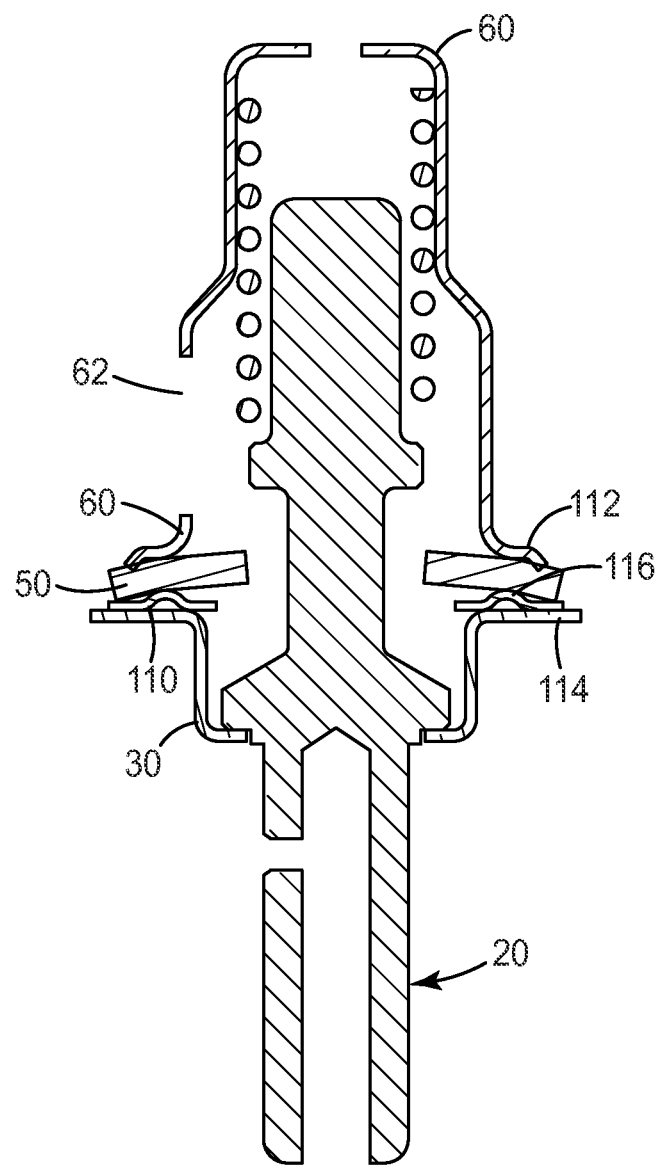
FIG. 9 shows a cross-section through part of a sixth embodiment of an exemplary valve according to the present invention.

FIG. 9 shows another arrangement to tension the metering gasket (50) and thereby to accurately and consistently define its position. This embodiment is similar to that shown in FIG. 7, but uses flat rather than sloped (conical) flanges (112, 114) together with a washer (110) with a rounded bump (116).

Figure 10:
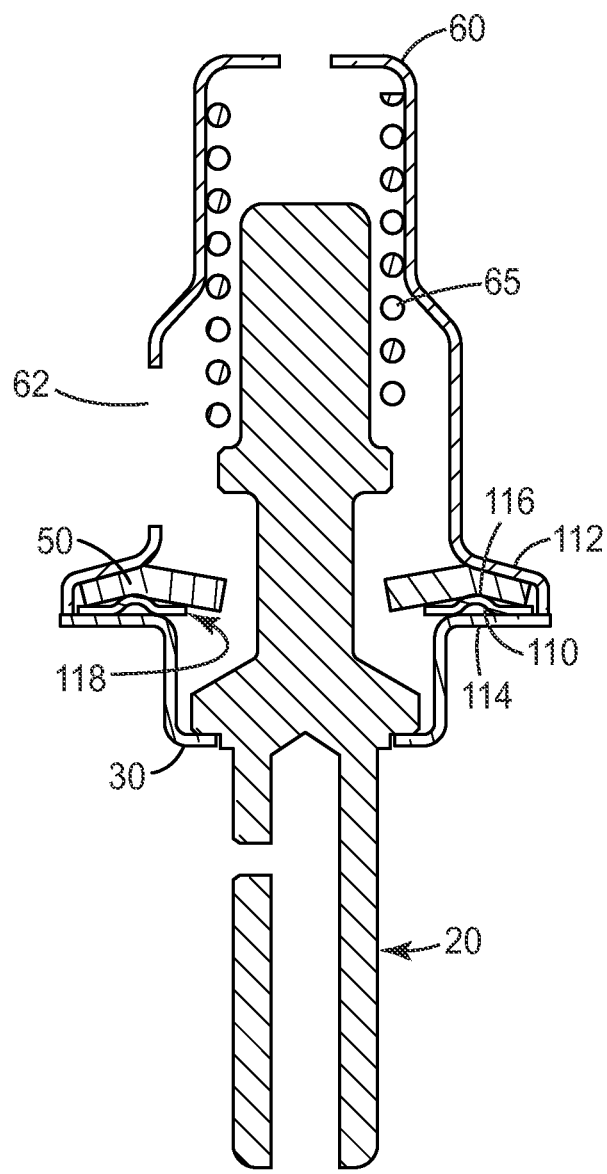
FIG. 10 shows a cross-section through part of a seventh embodiment of an exemplary valve according to the present invention.

FIG. 10 shows another arrangement including a support washer (110) with a rounded bump (116). Here the flange (112) of the spring cage is extended, pushing the metering gasket down against the rounded bump in such a way as to cause the inner region of the metering gasket to sit reliably against the support offered by the washer (110) at its inner periphery (118). The bias imparted by the configuration shown ensures that the seal always returns to sit consistently against the inner periphery (118) of the washer (110).

Figure 11:
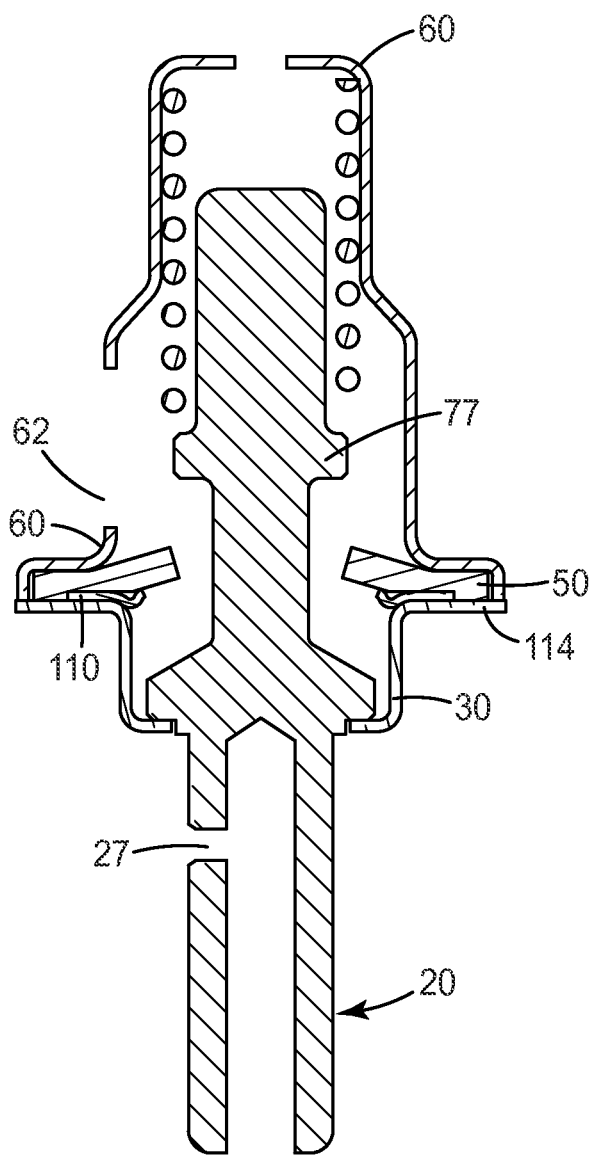
FIG. 11 shows a cross-section through part of an eighth embodiment of an exemplary valve according to the present invention.

FIG. 11 shows an alternative embodiment of the washer (110) of FIG. 4. In this case, the outer diameter of the washer is reduced, in order to allow the metering gasket (50) to seal directly onto the flange (114) of the valve body, thereby eliminating any possibility of a transient leakage path. In order to allow the washer to now be centred correctly and concentrically during assembly, the washer is bent into a shape that can centre itself in the top of the bore of the valve body (30). It will be noted that the outermost edge of the washer acts as a sealing bead to prevent seal "walk out".

Figure 12:
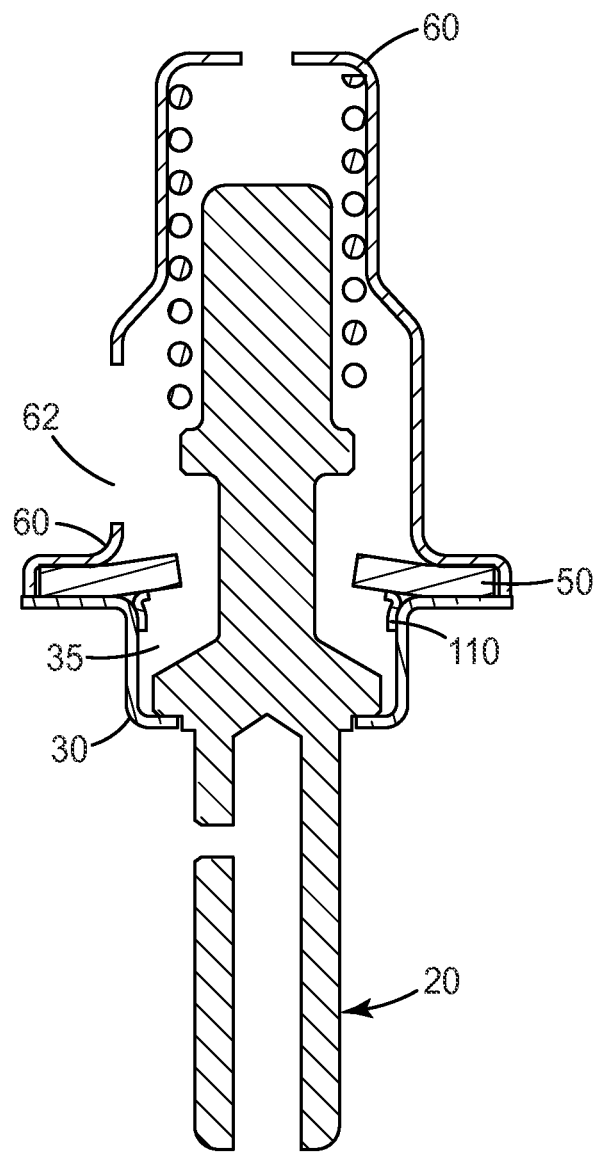
FIG. 12 shows part of a variation of the eighth embodiment.

FIG. 12 shows another possible modification of the embodiment shown in FIG. 4. In this embodiment, the washer (110) is centred on the top of the bore of the valve body in an alternative manner, held by an interference fit with the valve body. As with the embodiment of FIG. 11, the reduced outer diameter of the washer (110) means that any potential transient leakage path as discussed in conjunction with the embodiment shown in FIG. 4 is avoided.

Figure 13:
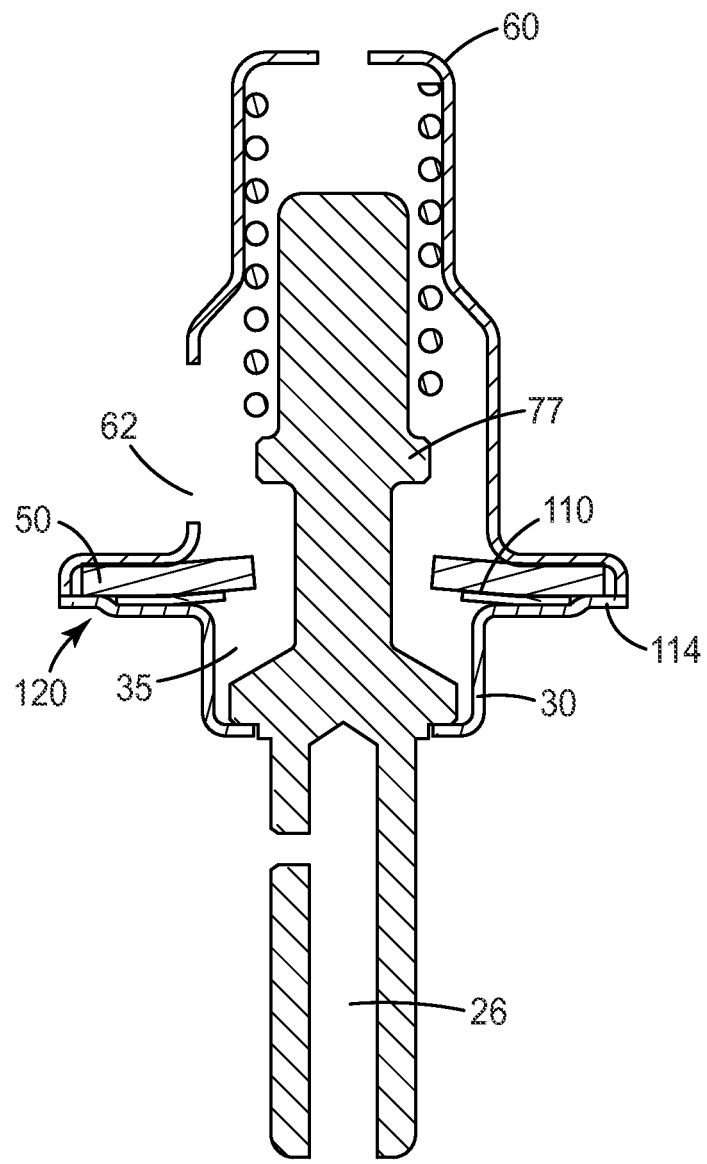
FIG. 13 shows a cross-section through part of a ninth embodiment of an exemplary valve according to the present invention.

FIG. 13 shows a further embodiment of the present invention, incorporating a support washer (110) to force the metering gasket (50) to adopt a single inward positional mode. The washer, having a reduced outer diameter as in the embodiments shown in FIGS. 11 and 12, is centred by a step (120) on the flange (114) of the valve body (30). The reduced washer outer diameter again avoids any potential of a transient leakage path as the metering gasket (50) seals directly against the valve body flange (114), and the outermost edge of the washer acts as a sealing bead to prevent seal "walk out".

Figure 14:
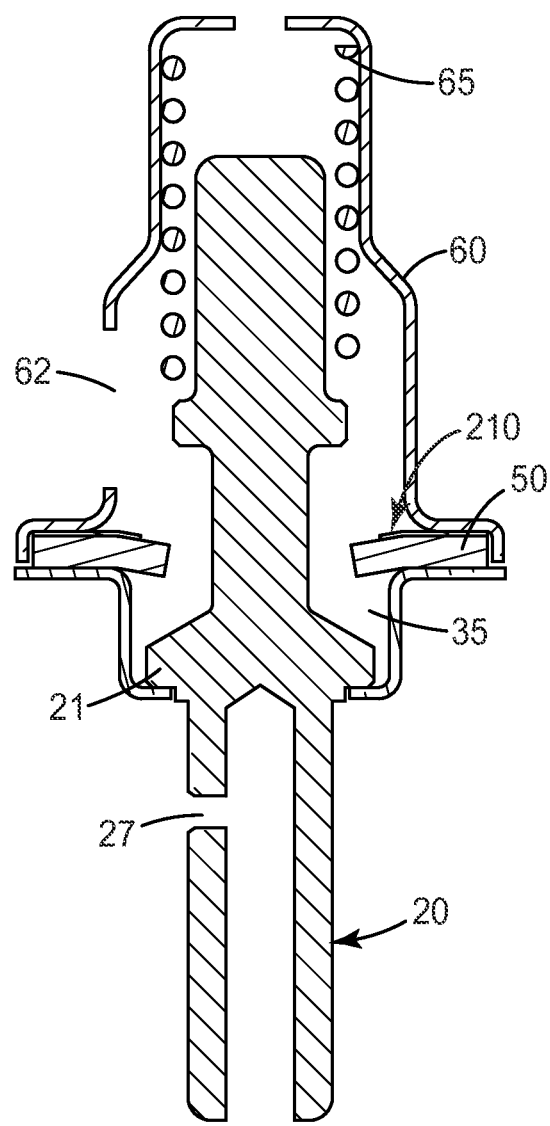
FIG. 14 shows a cross-section through part of a tenth embodiment of an exemplary valve according to the present invention.

FIG. 14 shows a further embodiment of this invention in which the metering gasket is biased outwardly by a thin shim spring (210) provided on the opposite side of the metering gasket to the washer shown in FIG. 4. In other words the thin shim spring is positioned between the upper surface of the metering gasket and the lower surface of the flange of the spring cage. Such a spring (e.g. in the form of a washer or bent washer or skeletal shim) is flexible enough to bend readily under the force applied by the patient to the valve stem, in order to allow the metering gasket to deflect as the stem pushes against it, while being resilient enough to return the metering gasket reliably to its rest position after completion of the valve actuation.

Figure 15:
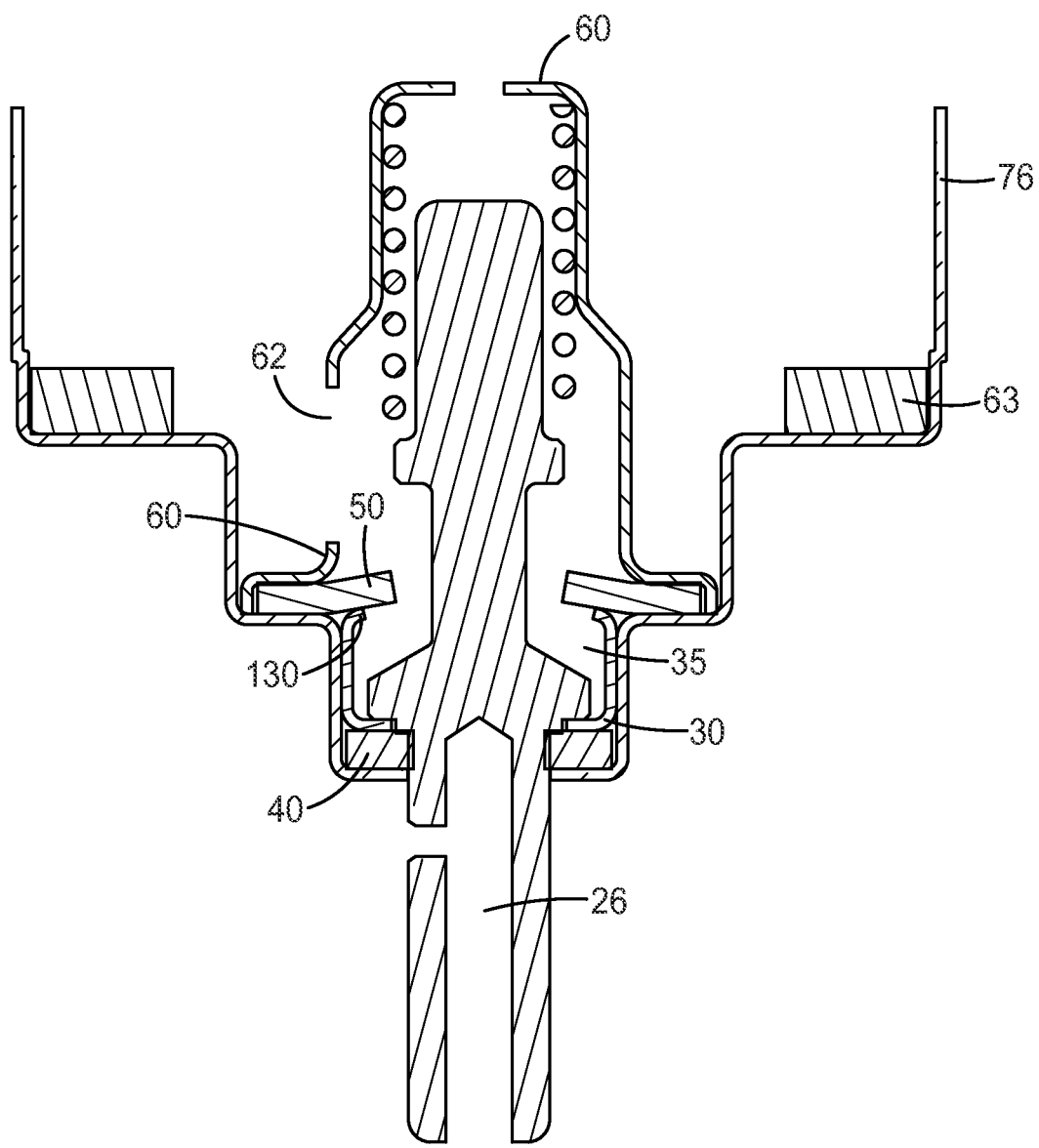
FIG. 15 shows a cross-section through an eleventh embodiment of an exemplary valve according to the present invention.

FIG. 15 shows another embodiment of the present invention, wherein the upper edge of the valve body (30) is bent backwards on itself in order to provide a supporting surface (130) for the metering gasket, said supporting surface functioning similarly to the washer shown in the embodiment shown in FIG. 4 but again without the need for a separate washer and without the possibility of a transient leakage path. Axial alignment of the curved or angled upper edge of the valve body with the adjacent shoulder of the ferrule can be optimized for optimal metering gasket location and positional control.

Figure 16:
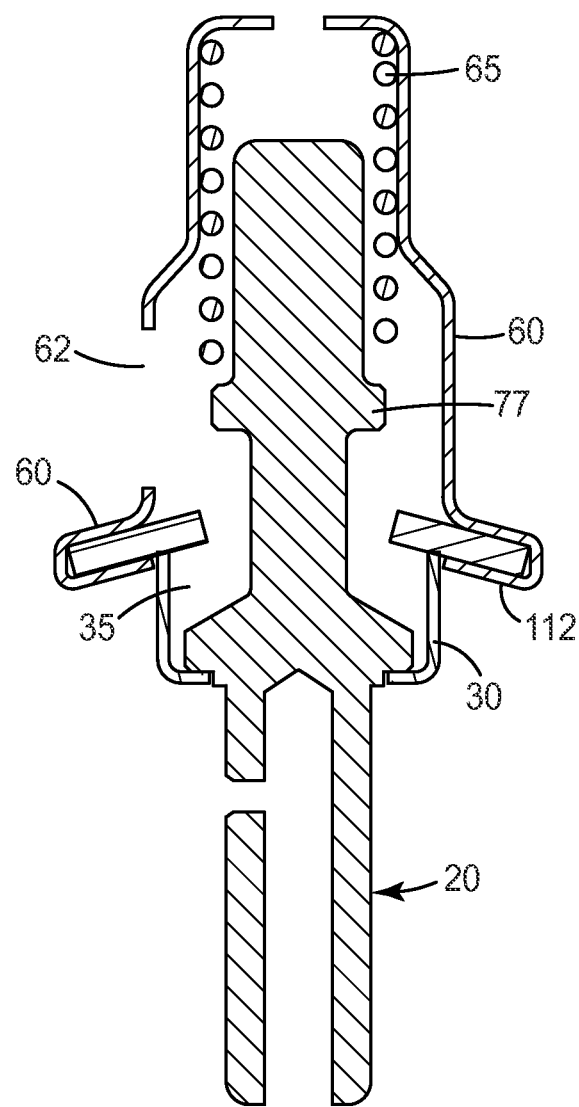
FIG. 16 shows a cross-section through part of a twelfth embodiment of an exemplary valve according to the present invention.

FIG. 16 shows a further embodiment similar to that shown in FIG. 8A, where the spring cage (60) is provided with a substantially, angled U-shape (in its longitudinal cross-section) so that the metering gasket (50) is biased inwardly. The upper edge of the valve body (30) provides further positional support for the metering gasket.

Figure 17:
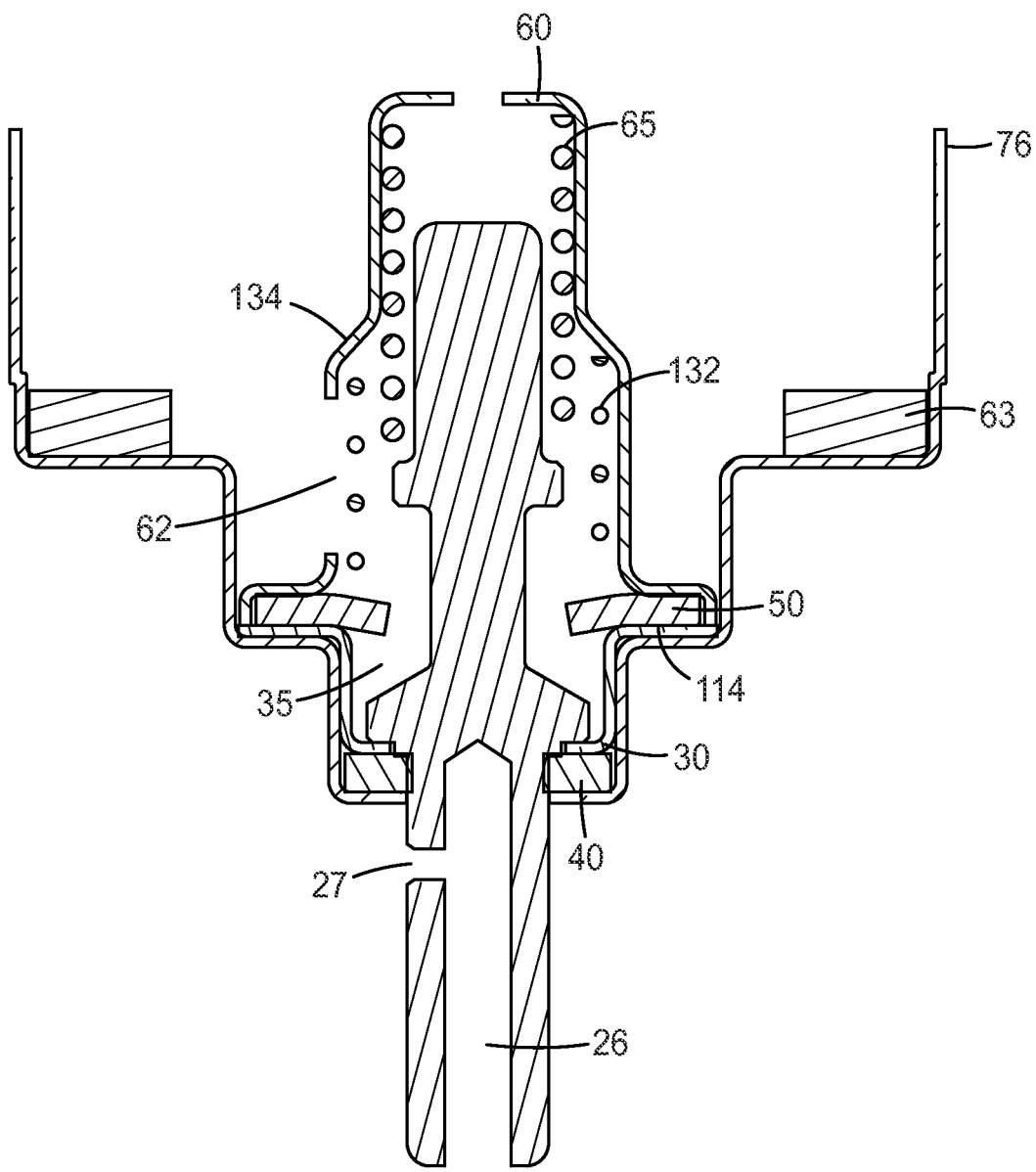
FIG. 17 shows a cross-section through a thirteenth embodiment of an exemplary valve according to the present invention.

FIG. 17 shows another embodiment of this invention, in which the metering gasket is biased outwardly though the inclusion of a second compression spring (132) thereby removing a risk of metering gasket positional uncertainty or bimodality. The second compression spring is selected so as to lightly push the metering gasket (50) against the upper flange (114) of the valve body (30) when the valve is in its rest position. The top end of the spring sits against a step (134) on the spring cage bore, the lower end against the upper side of the metering gasket. The spring is preferably a light metal coil spring, but could be made of plastic material.

Figure 18:
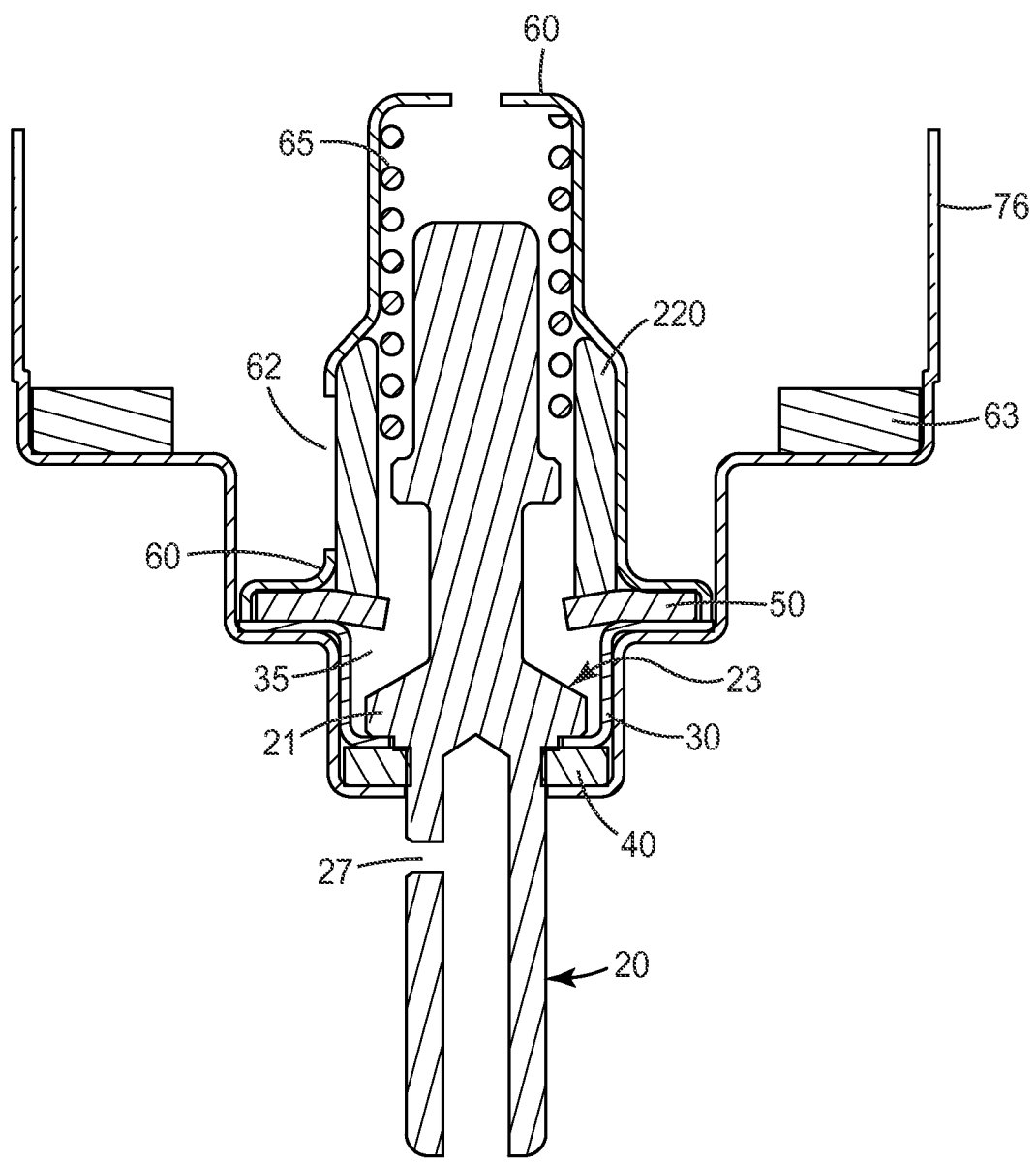
FIG. 18 shows a cross-section through a fourteenth embodiment of an exemplary valve according to the present invention.

FIG. 18 shows a variation on the embodiment shown in FIG. 17. In this embodiment a piece of fluid permeable particle semi-permeable material (220) (e.g. an open cell foam) as described in International Patent Application no. PCT/US2007/073764 is used in place of the second spring, serving the dual functions of removing any potential metering gasket bimodality and also improving the sampling of suspension formulations.

Figure 19:
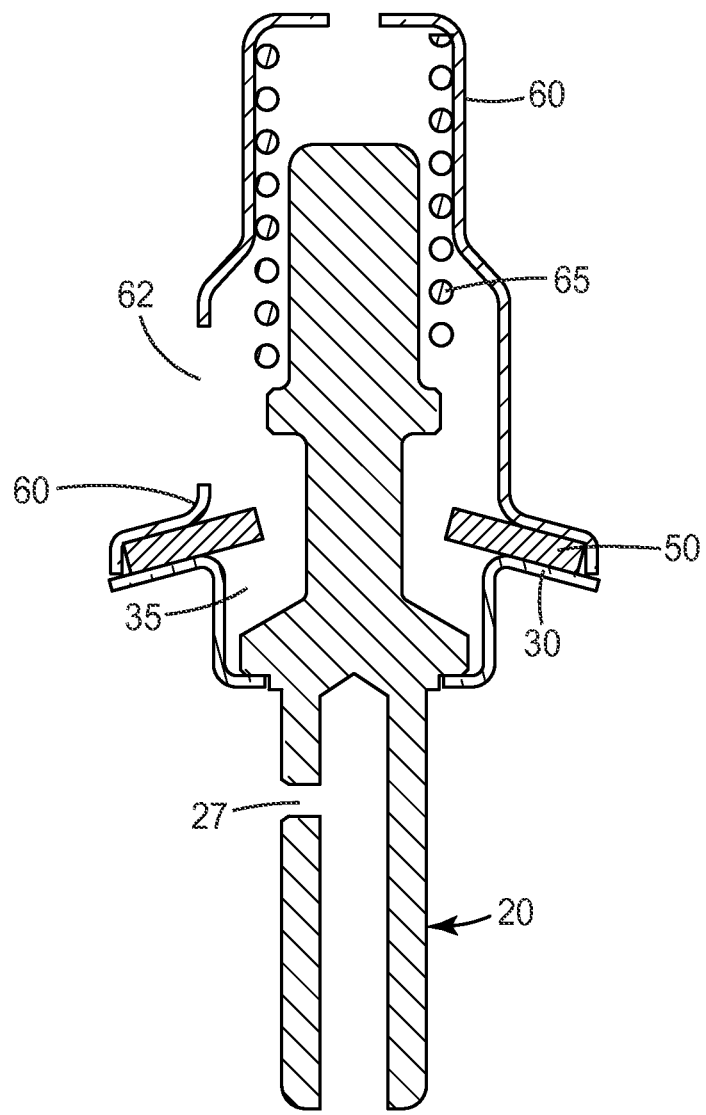
FIG. 19 shows a cross-section through part of a fifteenth embodiment of an exemplary valve according to the present invention.

The embodiment shown in FIG. 19 represents a further variation on the embodiments of FIGS. 8 and 11, and uses a modified profile of valve body (30) to provide the function of the washer of the embodiment shown in FIG. 4 without the need for such a separate washer.

Figure 20A:
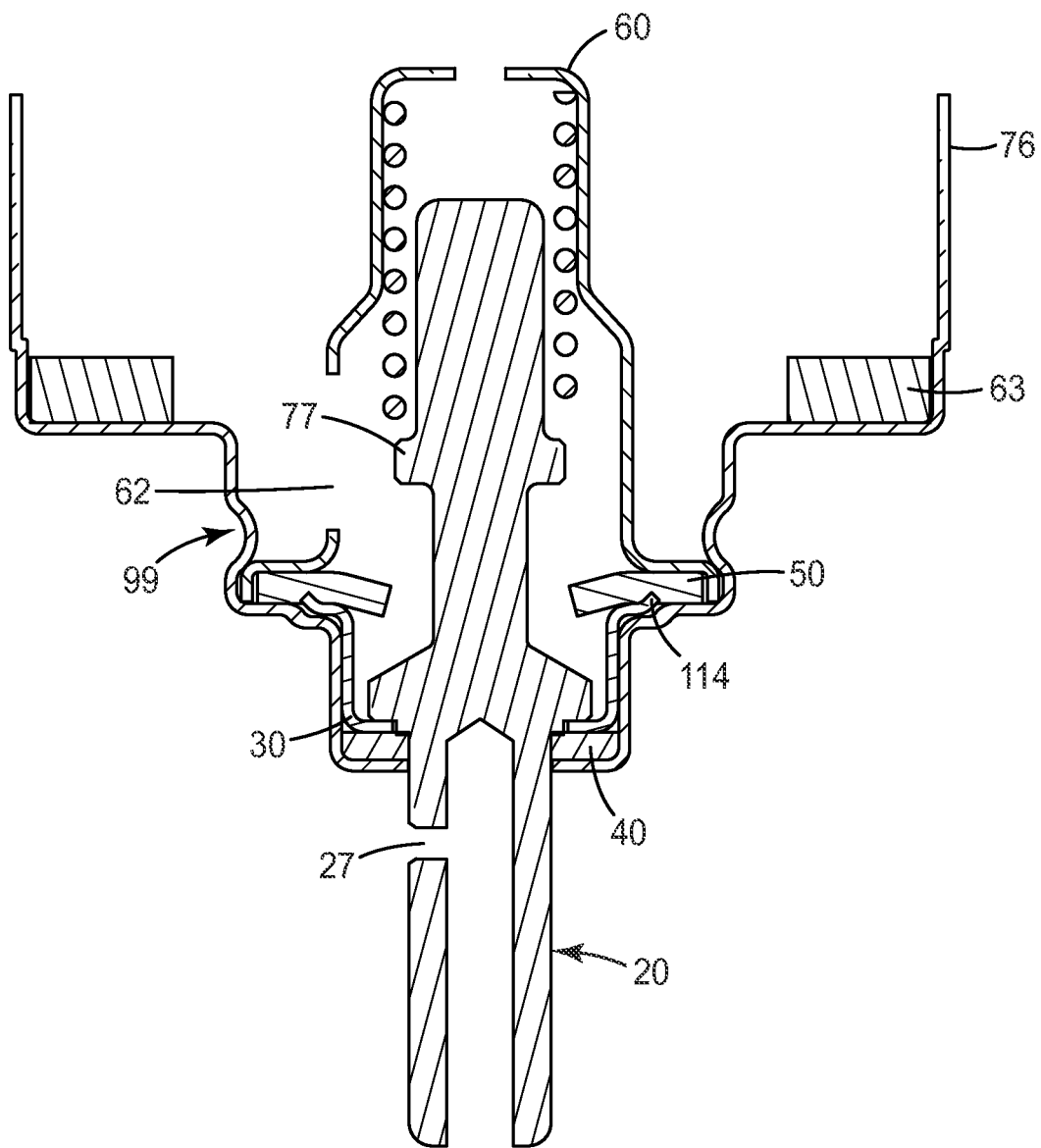
FIG. 20 shows a cross-section through three exemplary variants (FIGS. 20a, 20b and 20c) of a sixteenth embodiment of a valve according to the present invention.
Figure 20B:
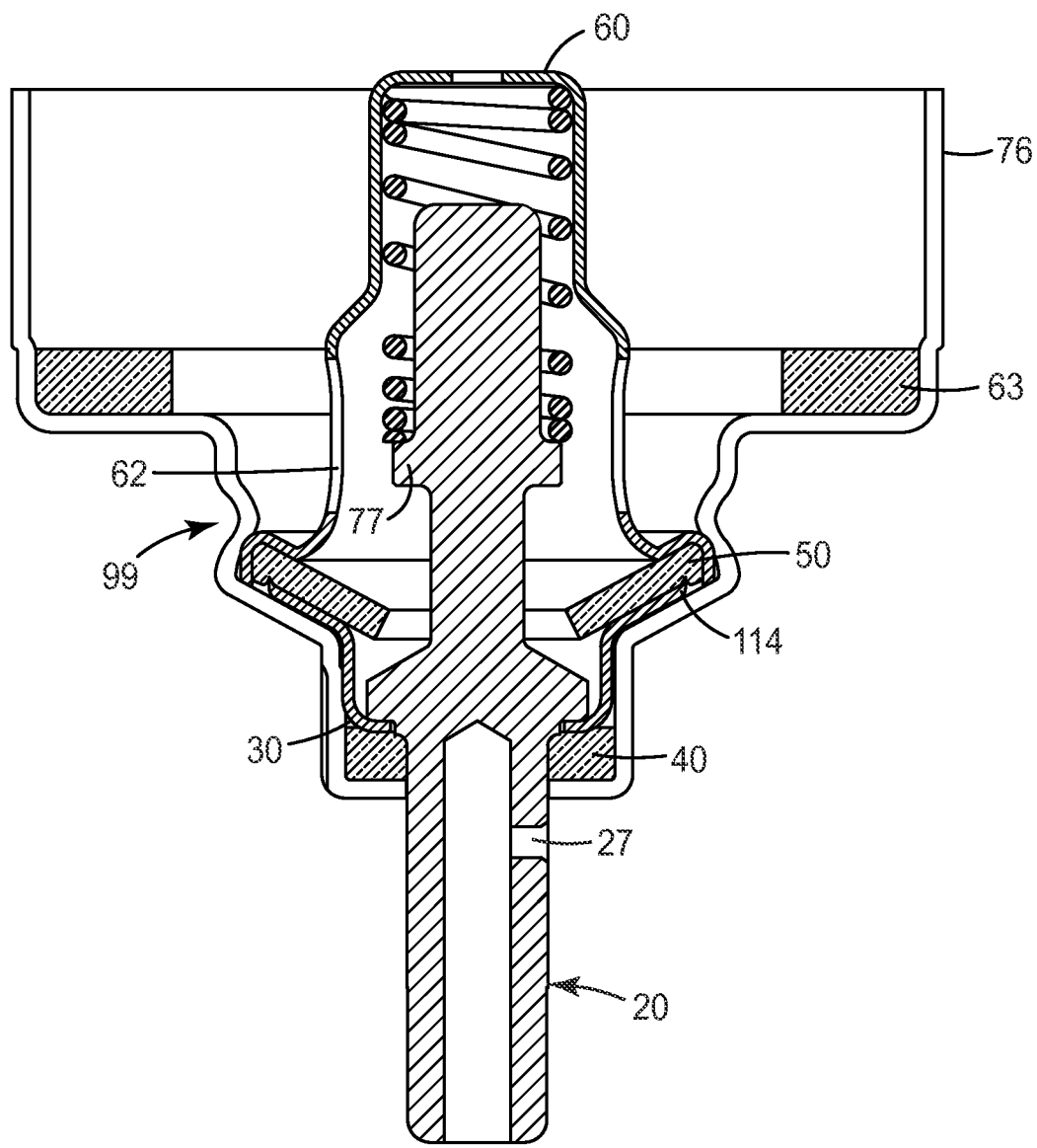
Figure 20C:
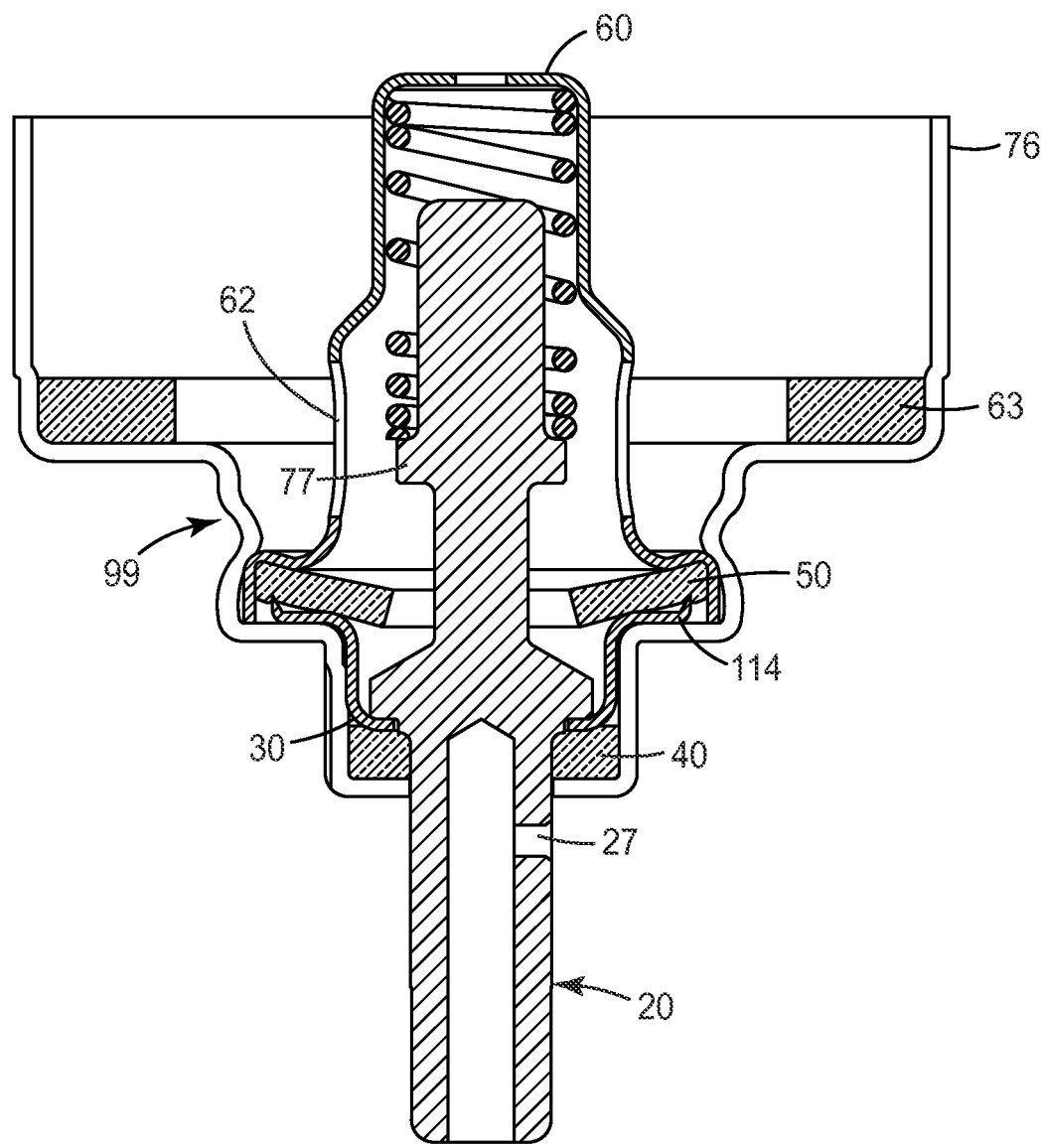

FIG. 20 shows three exemplary variants (FIGS. 20a, 20b and 20c) of an embodiment in which the flange (114) of the valve body is reduced in diameter and its edges are angled or curved upwards to grip the metering gasket (50) and to urge the inner periphery of the metering gasket out of a substantially planar form (e.g. to stretch and/or bias it outwardly in order to avoid potential positional/directional bimodality). This arrangement also serves to grip the metering gasket to prevent it getting dragged or "walked" out during pressure filling and/or valve operation. Gripping and stretching of the metering gasket to urge its inner periphery out of a substantially planar form and to prevent it getting dragged out is further facilitated by the edge of the flange (114) of the valve body being formed and clipped in such a way as to give it a sharp edge, e.g. as shown in the variants illustrated in FIGS. 20b and 20c. It will be noted that the edge of the flange of the spring cage (60) contacts the valve ferrule (76). This metal to metal contact provides a well-defined depth of circumferential recess in which the metering gasket is located, in analogous manner to the provision of a circumferential recess between the spring cage and the valve body flange in the embodiments of the present invention shown in FIGS. 4, 11, etc. In the exemplary variants shown in FIGS. 20b and 20c, e.g. in comparison to the variant shown in FIG. 20a, it will also be appreciated that the spring cage is formed so as to provide a cone angle, thus further facilitating the urging of the inner periphery of the metering gasket out of a substantially planar form. For ease in viewing, the illustrated cone angles of the spring cage and correspondingly the cone angles of the metering gasket in FIGS. 20b and 20c are exaggerated. Again mentioned above, FIG. 20 illustrates the position of the crimp (99) in the ferrule used to hold this valve together. Desirably, similar crimping is used (but is not shown) in all the other valve embodiments shown herein.

Figure 21:
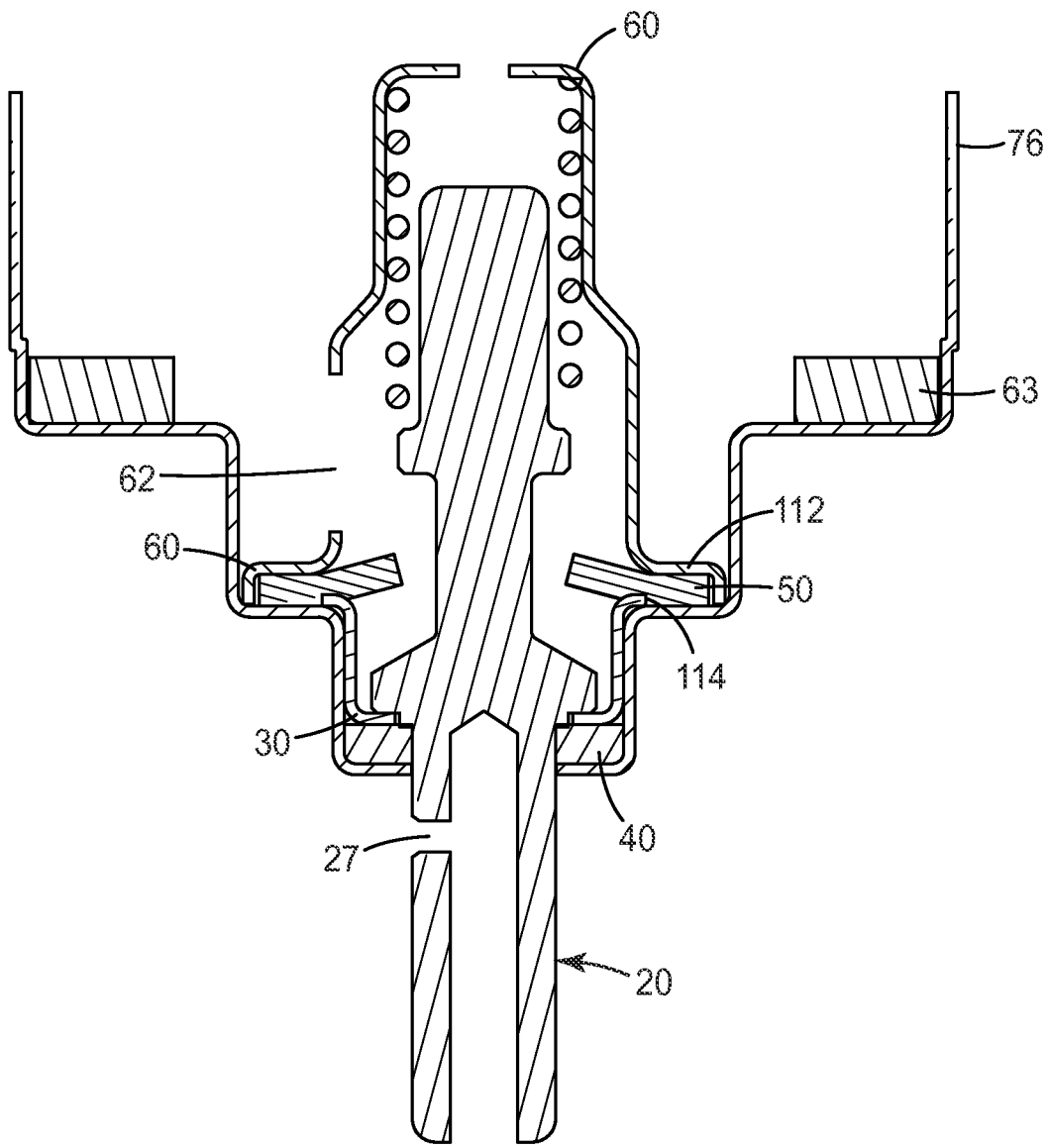
FIG. 21 shows a variation of the embodiment shown in FIG. 20.

FIG. 21 illustrates a variation of the principle shown in FIG. 20, wherein the edge of the valve body flange (114) is reduced in diameter so that it serves to grip the metering gasket. In this case, unlike in FIG. 20, the edge and/or any burr on it serves to grip the seal (e.g. by providing a "sealing bead") without the edge of the valve body flange (114) being bent or curved upwards. The position of the edge relative to the position of the flange (112) of the spring cage (60) is such that it tends to apply an inward positional bias to the metering gasket, again minimizing any risk of positional bimodality.

Figure 22:
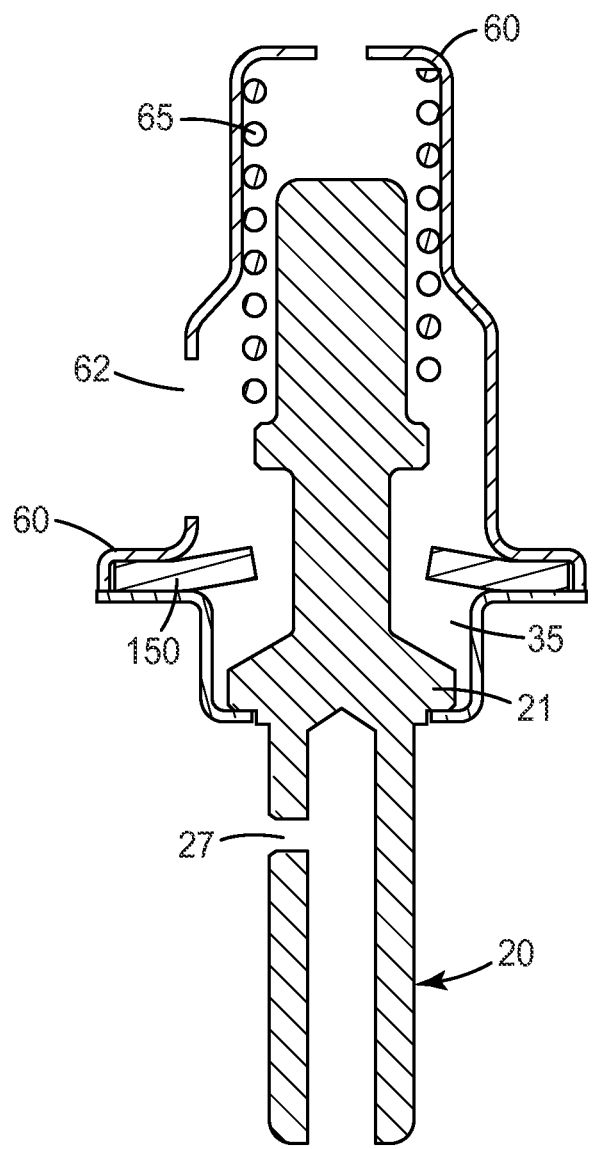
FIG. 22 shows a cross-section through part of a further embodiment of an exemplary valve according to the present invention.

FIG. 22 shows an embodiment of valve in which a metering gasket (150) is pre-biased into a single bent or curved mode, preferably with its convex central region towards the spring cage, by pre-stressing or pre-doming the metering gasket in order to pre-bias it into a dished shape prior to valve assembly. Such pre-biasing can involve stamping flat seals and then shaping them, e.g. by the application of force and/or heat. Alternatively metering gaskets may be sliced from an extruded tube and post-domed, or internal stresses can be created within the tube in such a way that subsequently sliced annular metering gaskets adopt a one-way dished or domed shape. Such dish-shaped metering gaskets avoid positional bimodality. Preferably such dish-shaped metering gaskets are made of a shape-memory polymer, more preferably a shape-memory elastomer.

Figure 23:
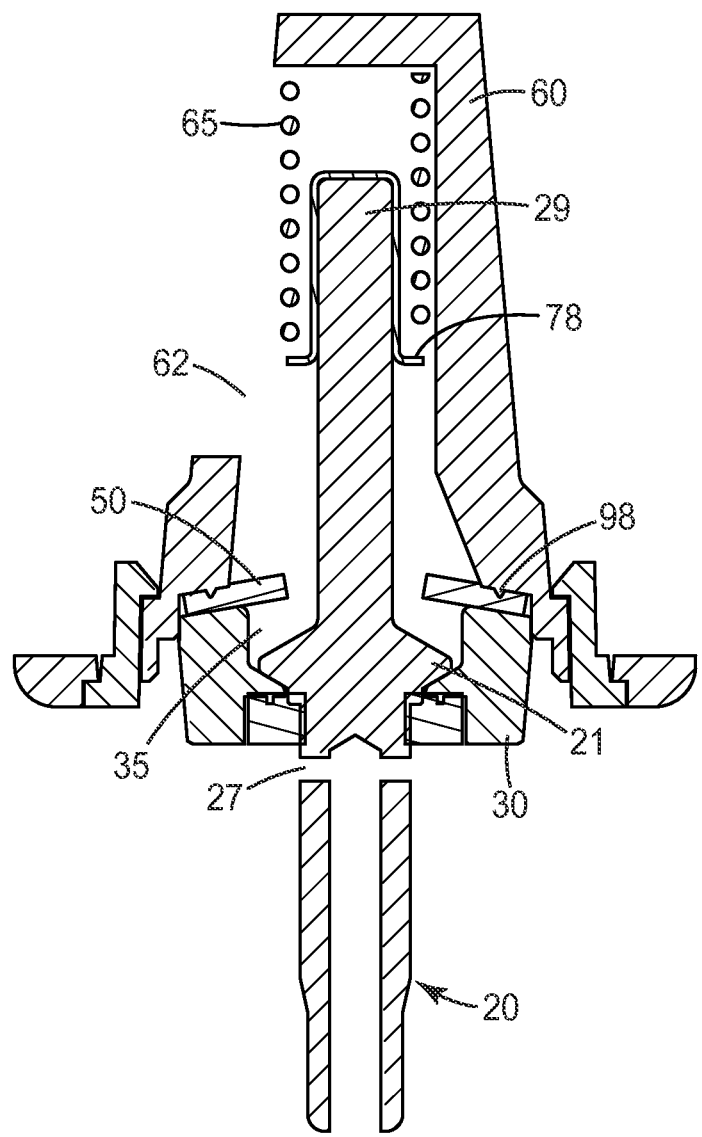
FIG. 23 shows a cross-section through part of yet a further embodiment of an exemplary valve according to the present invention.

FIG. 23 shows another embodiment of this invention in which a frusto-conical (angled, as seen in longitudinal cross-sections of the valve) recess is provided for the metering gasket (50) between the valve body (30) and the spring cage (60) components. The spring cage (60), valve body (30) and valve stem (20) of this embodiment are suitably plastic injection mouldings. This arrangement serves to hold the metering gasket in a consistent position, biased inwardly, when the valve stem (20) is in its at-rest position. A small annular sealing bead (98) on the underside of the spring cage (60) serves to help to grip the metering gasket (50) and hold it against any possibility of "walk-out" during valve operation. Although not shown in the illustration the valve would include a valve ferrule.

Figure 24:
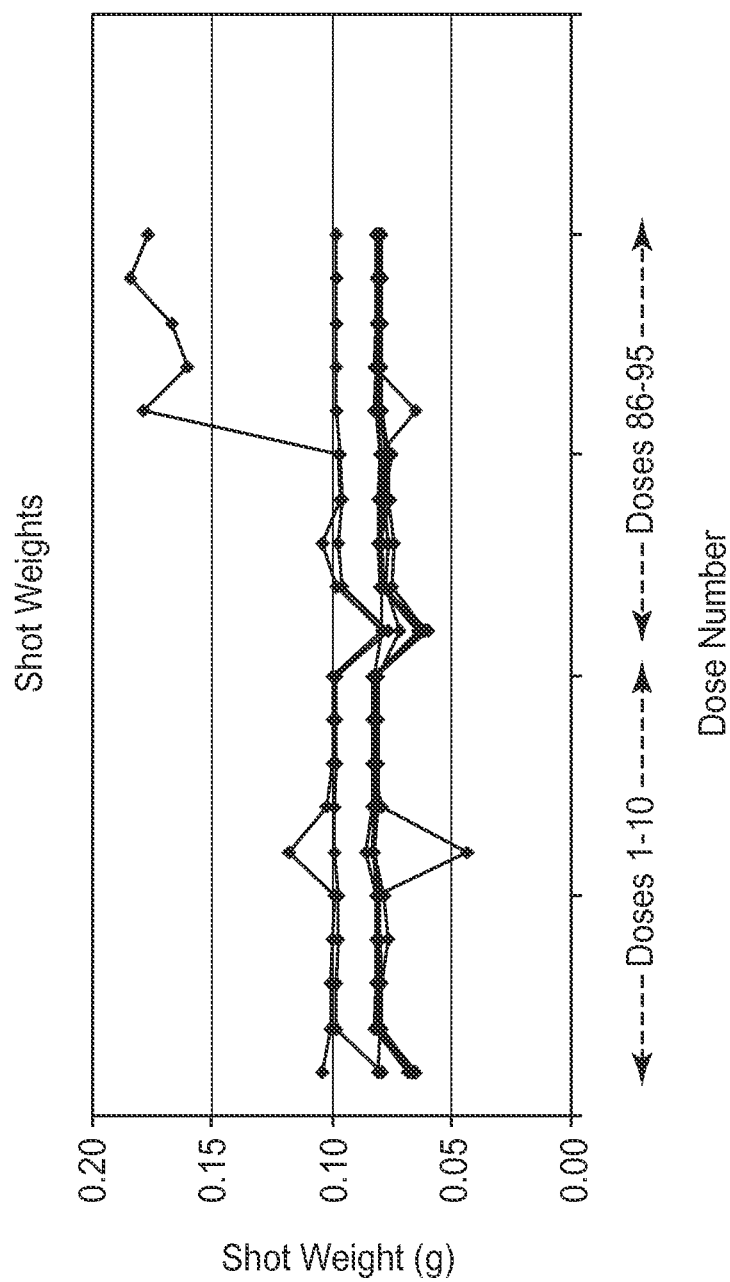
FIG. 24 shows shot weight data obtained using a known design of valve.

FIG. 24 shows shot (dose) weight data from one set of ten dispensers each fitted with a face-seal type pMDI valve where the metering gasket was unbiased and configured to be planar, i.e. perpendicular to the axis of the valve stem. Clear bimodality problems are seen with the shot weights, with a majority of valves showing a low shot weight mode (believed to correspond to the metering gasket sitting "randomly" outwardly) and with two nominally identical valves showing a higher shot weight mode (believed to correspond to the metering gasket sitting "randomly" inwardly). In one of the latter two valves, mid-way streaming occurred later in life. This is presumed to have been caused by the metering gasket sitting too far inwardly from its design position, perhaps as a result of partial gasket "walk out", after a number of operating cycles, so that the side hole of the valve stem passed the diaphragm seal before the face seal was made between the metering gasket and the sealing surface of the valve stem. Both seals were thus temporarily bypassed at the same time, leading to streaming of formulation out of the valve, and hence excessive shot weights, midway through the stem's travel.

FIG. 25 shows shot weight data from 20 valves fitted with an angled washer of the type shown in FIG. 4. In these valves, the washers were made from stainless steel of 0.005" (0.13 mm) thickness, each washer having an outer diameter of 0.427" (10.8 mm) and an inner diameter of 0.207" (5.3 mm), and with the part of the washer within a diameter of 0.300" (7.6 mm) being angled at approximately 6° upwards (inwards in the valve) from that diameter. (All dimensions are approximate.) Of approximately 1100 shots, there were no "fliers" of unusually high or low shot weight and there was no evidence for any metering gasket positional bimodality.

In the light of the described embodiments, modifications of these embodiments, as well as other embodiments, all within the scope of the present invention, will now become apparent to persons skilled in the art.

The invention claimed is:

1. An aerosol metering valve comprising:
   (a) a valve stem movable between a rest position and a firing position comprising:
      a body portion comprising a circumferential sealing surface
   (b) a valve body comprising:
      a body wall, and
      an internal chamber defined at least in part by the body wall; and
   (c) a metering gasket having an inner periphery defining an aperture, being disposed near the most interior end of the internal chamber and being configured to be able to form a transient, substantially fluid-tight face seal against the circumferential sealing surface of the valve stem,
   where at the rest position of the valve stem, the body portion of the valve stem is located within the internal chamber and as the valve stem is moved from its rest position towards its firing position the circumferential sealing surface of the valve stem contacts the metering gasket to form a face seal thereby closing a metering chamber and thereafter further movement of the valve stem towards its firing position causes the metering gasket to deflect while maintaining the seal with the circumferential sealing surface of the valve stem; and
   wherein the metering gasket in an unbiased configuration is an annular disc having a substantially planar form and where the valve comprises at least one biasing structure constructed and arranged such that the biasing structure urges the inner periphery of the metering gasket out of said substantially planar form at the rest position of the valve stem, and wherein, at the rest position of the valve stem, the inner periphery of the metering gasket is positioned towards the body portion of the valve stem.

2. An aerosol metering valve comprising:
   (a) a valve stem movable between a rest position and a firing position comprising:
      a body portion comprising a circumferential sealing surface
   (b) a valve body comprising:
      a body wall, and
      an internal chamber defined at least in part by the body wall; and
   (c) a metering gasket having an inner periphery defining an aperture, being disposed near the most interior end of the internal chamber and being configured to be able to form a transient, substantially fluid-tight face seal against the circumferential sealing surface of the valve stem, where at the rest position of the valve stem, the body portion of the valve stem is located within the internal chamber and as the valve stem is moved from its rest position towards its firing position the circumferential sealing surface of the valve stem contacts the metering gasket to form a face seal thereby closing a metering chamber and thereafter further movement of the valve stem towards its firing position causes the metering gasket to deflect while maintaining the seal with the circumferential sealing surface of the valve stem; and wherein the metering gasket in an unbiased configuration is an annular disc having a substantially planar form and where the valve comprises at least one biasing structure constructed and arranged such that the biasing structure urges the inner periphery of the metering gasket out of said substantially planar form at the rest position of the valve stem, and wherein, at the rest position of the valve stem, the inner periphery of the metering gasket is positioned towards the body portion of the valve stem and further wherein the outer periphery of a major surface of the metering gasket towards the body portion of the valve stem is pulled radially outwards into tension.

\* \* \* \* \*

UNITED STATES PATENT AND TRADEMARK OFFICE
CERTIFICATE OF CORRECTION

| | |
|---|---|
| PATENT NO. | : 8,814,009 B2 |
| APPLICATION NO. | : 12/681280 |
| DATED | : August 26, 2014 |
| INVENTOR(S) | : Peter Hodson |

It is certified that error appears in the above-identified patent and that said Letters Patent is hereby corrected as shown below:

SPECIFICATION

COLUMN 10
Line 65, Delete "20°'" and insert -- 20°) --, therefor.

Signed and Sealed this
Fifth Day of May, 2015

Michelle K. Lee
*Director of the United States Patent and Trademark Office*